United States Patent
Yoshimoto et al.

(10) Patent No.: US 8,932,393 B2
(45) Date of Patent: *Jan. 13, 2015

(54) AZO COMPOUND, INK COMPOSITION, RECORDING METHOD AND COLORED MATERIAL

(75) Inventors: Takashi Yoshimoto, Tokyo (JP); Akira Kawaguchi, Tokyo (JP); Kenji Ooshima, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/993,599

(22) PCT Filed: Dec. 14, 2011

(86) PCT No.: PCT/JP2011/078959
§ 371 (c)(1),
(2), (4) Date: Aug. 23, 2013

(87) PCT Pub. No.: WO2012/081640
PCT Pub. Date: Jun. 21, 2012

(65) Prior Publication Data
US 2013/0321523 A1 Dec. 5, 2013

(30) Foreign Application Priority Data
Dec. 17, 2010 (JP) .................................. 2010-281297

(51) Int. Cl.
| | | |
|---|---|---|
| C09D 11/02 | (2014.01) | |
| C09B 31/30 | (2006.01) | |
| C09D 11/328 | (2014.01) | |
| C07D 471/04 | (2006.01) | |

(52) U.S. Cl.
CPC ............ *C09D 11/328* (2013.01); *C07D 471/04* (2013.01); *C09B 31/30* (2013.01)
USPC .......................... 106/31.48; 534/752; 534/754

(58) Field of Classification Search
USPC ................................. 106/31.48; 534/752, 754
See application file for complete search history.

(56) References Cited

U.S. PATENT DOCUMENTS

| | | | | |
|---|---|---|---|---|
| 5,447,819 | A  * | 9/1995 | Mooberry et al. | 430/226 |
| 7,217,803 | B2 * | 5/2007 | Feiler et al. | 534/752 |
| 7,326,288 | B2 * | 2/2008 | Matsui et al. | 106/31.52 |
| 7,901,498 | B2 * | 3/2011 | Hirota et al. | 106/31.5 |
| 8,080,100 | B2 * | 12/2011 | Yoshimoto et al. | 106/31.48 |
| 8,167,991 | B2 * | 5/2012 | Matsui et al. | 106/31.48 |
| 8,556,406 | B2 * | 10/2013 | Yoshimoto et al. | 106/31.5 |
| 2013/0257974 | A1 * | 10/2013 | Kawaguchi et al. | 347/20 |
| 2013/0335490 | A1 * | 12/2013 | Nagao et al. | 106/31.48 |

FOREIGN PATENT DOCUMENTS

| | | |
|---|---|---|
| DE | 2004488 A | 8/1971 |
| JP | H01-284562 | 11/1989 |
| JP | H05-018955 B | 3/1993 |
| JP | 3383469 B | 12/2002 |
| JP | 2006-509068 A | 3/2006 |
| JP | 2008-169374 A | 7/2008 |
| JP | 2009-263513 | 11/2009 |
| WO | WO 2004/050768 | 6/2004 |
| WO | WO 2005/054374 | 6/2005 |
| WO | WO 2007/077931 | 7/2007 |
| WO | WO 2008/056626 | 5/2008 |
| WO | WO 2009/069279 | 6/2009 |
| WO | WO 2010/143610 | 12/2010 |
| WO | WO 2012/081637 A1 * | 6/2012 |

OTHER PUBLICATIONS

English translation of JP 2009/263513; Nov. 2009.*
Processing technology, vol. 31, No. 9, pp. 599-602, 1996.

* cited by examiner

*Primary Examiner* — Helene Klemanski
(74) *Attorney, Agent, or Firm* — Knobbe Martens Olson & Bear LLP

(57) ABSTRACT

A coloring matter which exhibits excellent (ozone) gas resistance, high print density, low color rendering properties, low color saturation, and high-quality black hue when is recorded on a paper only for inkjet exclusive use, i.e., an azo compound represented by formula (1), a tautomer of the azo compound, or a salt of the azo compound or the tautomer; and an ink composition containing the coloring matter, particularly a black ink composition for inkjet recording applications.

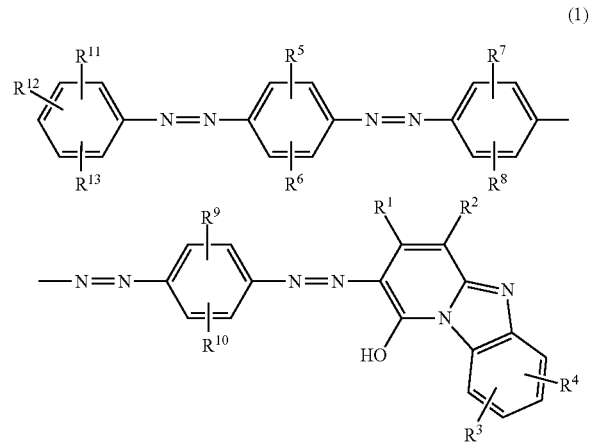

17 Claims, No Drawings

AZO COMPOUND, INK COMPOSITION, RECORDING METHOD AND COLORED MATERIAL

This application is the U.S. National Phase under 35 U.S.C. §371 of International Application PCT/JP2011/078959, filed Dec. 14, 2011, designating the U.S., and published in Japanese as WO 2012/081640 on Jun. 21, 2012, which claims priority to Japanese Patent Application No. 2010-281297, filed Dec. 17, 2010, the entire contents of which are incorporated herein by reference.

TECHNICAL FIELD

The present invention relates to a novel azo compound or a tautomer thereof, or a salt of the azo compound or the tautomer, an ink composition containing the azo compound, the tautomer, or the salt, and a colored material colored with the azo compound, the tautomer, or the salt.

BACKGROUND ART

A recording method using an inkjet printer, that is, an inkjet recording method, is a representative method among various color recording methods. An inkjet recording method is to perform recording by generating small ink droplets and attaching the ink droplets to a variety of record-receiving materials (paper, film, cloth, and the like). In this method, since a recording head is not brought into direct contact with a record-receiving material, less noise is generated and silent recording is achieved. Furthermore, since this method has the feature that it is easy to reduce apparatus size and to increase process speed, the inkjet recording method has been rapidly popularized in recent years, and further growth in the future is expected as well.

Conventionally, aqueous inks prepared by dissolving water-soluble dyes in an aqueous medium have been used as inks for fountain pens, felt pens, and the like and as inks for inkjet recording. These aqueous inks generally have water-soluble organic solvents added thereto so that clogging of the ink at pen tips or ink discharge nozzles can be prevented. Further, in regard to these inks, it is required that recorded images with sufficient densities be provided, that clogging at pen tips or nozzles not occur, that the inks have satisfactory dryability on record-receiving materials, that less bleeding occur, that the inks have excellent storage stability, and the like. Furthermore, the water-soluble dyes used therein are required to have high solubility, particularly in water, and to have high solubility in water-soluble organic solvents that are added to the inks. Moreover, the images thus formed are required to have image-fastness properties such as water resistance, light resistance, gas resistance, and moisture resistance.

Among these, gas resistance means resistance to a phenomenon of causing discoloration and fading of a recorded image via an action of ozone gas or the like present in the air and having an oxidizing action on a coloring matter in the record-receiving material. In addition to ozone gas, examples of oxidizing gases having this kind of action include NOx and SOx. However, among these oxidizing gases, ozone gas is regarded as the main causative substance that accelerates the phenomenon of discoloration and fading of inkjet-recorded images, and thus resistance to ozone gas in particular is considered important. At the surface of a paper for inkjet exclusive use capable of giving photographic-image quality, an ink-receiving layer is provided in order to speed up drying of the ink and to reduce bleeding at high image quality. Regarding the material of this ink-receiving layer, materials such as porous white inorganic substances are frequently used. On such a recording paper, discoloration and fading caused by ozone gas or the like is notably observed. Since this phenomenon of discoloration and fading caused by an oxidizing gas is characteristic of inkjet-recorded images, enhancement of gas resistance, particularly ozone-gas resistance, is one of the most important problems to be solved in the field of inkjet recording.

In order to extend the field of application of inkjet recording in the future, there is strong demand for further enhancements of light resistance, gas resistance, moisture resistance, water resistance, and the like in inkjet-recorded images. Furthermore, in addition to this, black images are required to have low color-rendering properties. The phenomenon in which hues seem to change depending on the type of light source is called color-rendering properties, and this phenomenon is likely to occur generally in black dyed materials or record materials. In the field of dye processing, it is common to use compounds having absorption at longer wavelengths in connection with methods for improving the color-rendering properties, and those methods are disclosed in, for example, Patent Documents 7 and 8, and Non-Patent Document 1.

Inks of various hues have been prepared from various coloring matters, but among them black ink is an important ink that is used in both monochromatic images and full-color images. Regarding the coloring matters for such black ink, a large number of coloring matters have been suggested to date; however, it has not been possible to provide coloring matters that adequately fulfill market demand. Many of coloring matters proposed are azo coloring matters, and among them disazo coloring matters such as C.I. Food Black 2 have problems such as poor water resistance or moisture resistance, insufficient light resistance and gas resistance, and high color-rendering properties. Polyazo coloring matters having an extended conjugated system have a problem in that the coloring matters generally have low water-solubility, a bronzing phenomenon in which recorded images partially have metallic gloss is likely to occur, and the coloring matters have insufficient light resistance and gas resistance. In addition, in the case of azo-containing metal coloring matters proposed similarly in large numbers, some have favorable light resistance, but there exist problems of safety for living organisms, unfavorable environmental influences due to metal ions included, extremely inferior ozone gas resistance, and the like.

Examples of black compounds (black coloring matters) for inkjet recording having improved gas resistance, which have been the most important problem to be solved in recent years, include the compounds described in Patent Document 1. These compounds have enhanced gas resistance, but still do not sufficiently fulfill market demand. Furthermore, azo compounds having a benzimidazolopyridone skeleton, which is one of the features of the black coloring matter of the present invention, are disclosed in Patent Documents 2 to 6 and the like. Patent Document 3 discloses trisazo compounds; however, these trisazo compounds have a symmetric structure in which two benzimidazolopyridone skeletons are bonded to the two ends of a linking group containing an azo structure, via another azo structure at each end of the linking group. Thus, compounds similar to the asymmetric azo compound of the present invention are not disclosed therein. Patent Documents 4 and 5 disclose the use of a trisazo compound and a water-soluble black compound for inkjet recording. Furthermore, Patent Document 6 discloses the use of a tetrakisazo compound and a water-soluble black compound for inkjet recording.

Patent Document 1: PCT International Publication No. WO2005/054374
Patent Document 2: PCT International Publication No. WO2004/050768
Patent Document 3: German Patent Application, No. 2004488, Specification Patent Document 4: PCT International Publication No. WO2007/77931
Patent Document 5: PCT International Publication No. WO2009/69279
Patent Document 6: Japanese Unexamined Patent Application, Publication No. 2008-169374
Patent Document 7: Japanese Unexamined Patent Application, Publication No. H01-284562
Patent Document 8: Japanese Patent Publication No. H05-018955
Patent Document 9: Japanese Patent Publication No. 3383469
Non-Patent Document 1: Processing technology, Vol. 31, No. 9, pp. 599-602, 1996.

DISCLOSURE OF THE INVENTION

Problems to be Solved by the Invention

An object of the present invention is to provide a coloring matter that exhibits, when recorded on a paper for inkjet exclusive use, superb (ozone) gas resistance, a very high print density, low color-rendering properties, and low color saturation, and has a high-quality black hue; and an ink composition, particularly a black ink composition for inkjet recording, containing the coloring matter.

Means for Solving the Problems

The inventors of the present invention conducted thorough investigations in order to solve problems such as those described above, and as a result the inventors found that a particular azo compound can solve the problems described above, thus completing the present invention.

Accordingly, a first aspect of the present invention provides an azo compound represented by the following formula (1), a tautomer thereof, or a salt of the azo compound or the tautomer:

$R^1$ represents a (C1-C4) alkyl group; a (C1-C4) alkyl group substituted with a carboxy group; a phenyl group; a phenyl group substituted with a sulfo group; or a carboxy group, $R^2$ represents a cyano group; a carbamoyl group; or a carboxy group, $R^3$ and $R^4$ each independently represent a hydrogen atom; a (C1-C4) alkyl group; a halogen atom; a (C1-C4) alkoxy group; or a sulfo group, $R^5$ represents a (C1-C4) alkylthio group; or a (C1-C4) alkylthio group substituted with at least one kind selected from the group consisting of a hydroxy group, a sulfo group, and a carboxy group, $R^6$ represents a (C1-C4) alkylcarbonylamino group, $R^7$ represents a (C1-C4) alkylthio group; or a (C1-C4) alkylthio group substituted with at least one kind of group selected from the group consisting of a hydroxy group, a sulfo group, and a carboxy group, $R^8$ represents a (C1-C4) alkylcarbonylamino group, $R^9$ and $R^{10}$ each independently represent a hydrogen atom; a carboxy group; a sulfo group; an acetylamino group; a chlorine atom; a (C1-C4) alkyl group; a (C1-C4) alkoxy group; or a (C1-C4) alkoxy group substituted with at least one kind of group selected from the group consisting of a hydroxy group, a (C1-C4) alkoxy group, a sulfo group, and a carboxy group, and $R^{11}$ to $R^{13}$ each independently represent a hydrogen atom; a carboxy group; a sulfo group; a hydroxy group; an acetylamino group; a chlorine atom; a cyano group; a nitro group; a sulfamoyl group; a (C1-C4) alkyl group; a (C1-C4) alkoxy group; a (C1-C4) alkoxy group substituted with at least one kind of group selected from the group consisting of a hydroxy group, a (C1-C4) alkoxy group, a sulfo group, and a carboxy group; a (C1-C4) alkylsulfonyl group; or a (C1-C4) alkylsulfonyl group substituted with at least one kind of group selected from the group consisting of a hydroxy group, a sulfo group, and a carboxy group, (1)

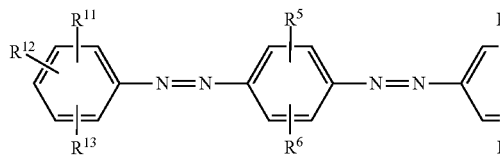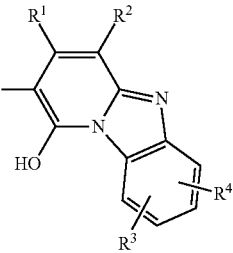

in the formula (1),

A second aspect of the present invention provides the azo compound, the tautomer thereof, or the salt of the azo compound or the tautomer according to the first aspect, where the azo compound represented by the formula (1) is represented by the following formula (2):

(2)

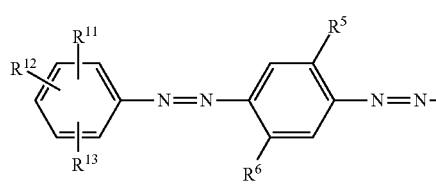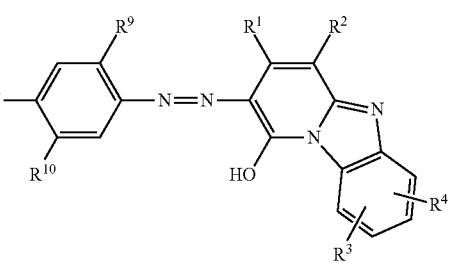

in the formula (2), $R^1$ to $R^{13}$ have the same meanings as respectively defined in formula (1).

A third aspect of the present invention provides the azo compound, the tautomer thereof, or the salt of the azo compound or the tautomer according to the first or second aspect, where in the formula (1) or (2), at least one of $R^{11}$ to $R^{13}$ represents a sulfo group; or a carboxy group, and at least one of $R^5$ to $R^{10}$ represents a (C1-C4) alkylthio group substituted with a sulfo group or a carboxy group; or a sulfo-(C1-C4) alkoxy group.

A fourth aspect of the present invention provides the azo compound, the tautomer thereof, or the salt of the azo compound or the tautomer according to any one of the first to third aspects, where in the formula (1) or (2), $R^5$ and $R^7$ each represent a (C1-C4) alkylthio group substituted with a sulfo group or a carboxy group; and $R^9$ represents a sulfo-(C1-C4) alkoxy group.

A fifth aspect of the present invention provides the azo compound, the tautomer thereof, or the salt of the azo compound or the tautomer according to any one of the first to fourth aspects, where in the formula (1) or (2), $R^1$ represents a methyl group; or a phenyl group, $R^2$ represents a cyano group; or a carbamoyl group, $R^3$ represents a hydrogen atom; a methyl group; or a methoxy group, and $R^4$ represents a sulfo group.

A sixth aspect of the present invention provides the azo compound, the tautomer thereof, or the salt of the azo compound or the tautomer according to the first or second aspect, where in the formula (1) or (2), $R^1$ represents a methyl group; or a phenyl group,
$R^2$ represents a cyano group; or a carbamoyl group,
$R^3$ represents a hydrogen atom; a methyl group; or a methoxy group,
$R^4$ represents a sulfo group,
$R^5$ represents a (C1-C4) alkylthio group substituted with a sulfo group or a carboxy group,
$R^6$ represents a (C1-C4) alkylcarbonylamino group,
$R^7$ represents a (C1-C4) alkylthio group substituted with a sulfo group or a carboxy group,
$R^8$ represents a (C1-C4) alkylcarbonylamino group,
$R^9$ represents a sulfo-(C1-C4) alkoxy group,
$R^{10}$ represents a (C1-C4) alkyl group; or an acetylamino group, and
$R^{11}$ to $R^{13}$ each independently represent a hydrogen atom; a carboxy group; a sulfo group; a chlorine atom; a nitro group; a methyl group; a methoxy group; a sulfamoyl group; or a (C1-C4) alkylsulfonyl group substituted with a sulfo group or a carboxy group.

A seventh aspect of the present invention provides the azo compound, the tautomer thereof, or the salt of the azo compound or the tautomer according to the first or second aspect, where in formula (1) or (2), $R^1$ represents a methyl group,
$R^2$ represents a cyano group or a carbamoyl group,
$R^3$ represents a hydrogen atom; a methyl group; or a methoxy group,
$R^4$ represents a sulfo group,
$R^5$ represents a sulfo-(C1-C4) alkylthio group,
$R^6$ represents a (C1-C4) alkylcarbonylamino group,
$R^7$ represents a sulfo-(C1-C4) alkylthio group,
$R^8$ represents a (C1-C4) alkylcarbonylamino group,
$R^9$ represents a sulfo-(C1-C4) alkoxy group,
$R^{10}$ represents a (C1-C4) alkyl group; or an acetylamino group, and
$R^{11}$ to $R^{13}$ each independently represent a hydrogen atom; a carboxy group; a sulfo group; a chlorine atom; a nitro group; a methyl group; a methoxy group; or a sulfamoyl group.

An eighth aspect of the present invention provides the azo compound, the tautomer thereof, or the salt of the azo compound or the tautomer according to the first or second aspect, where in formula (1) or (2), $R^1$ represents a methyl group;
$R^2$ represents a cyano group;
$R^3$ represents a hydrogen atom; or a methoxy group,
$R^4$ represents a sulfo group,
$R^5$ represents a sulfo-(C1-C4) alkylthio group,
$R^6$ represents an acetylamino group,
$R^7$ represents a sulfo-(C1-C4) alkylthio group,
$R^8$ represents an acetylamino group,
$R^9$ represents a sulfopropoxy group; or a sulfobutoxy group,
$R^{10}$ represents a (C1-C4) alkyl group,
$R^{11}$ represents a hydrogen atom; or a sulfo group,
$R^{12}$ represents a sulfo group; or a chlorine atom, and
$R^{13}$ represents a hydrogen atom; or a sulfo group.

A ninth aspect of the present invention provides an aqueous ink composition containing as a coloring matter, at least one kind of the azo compound, the tautomer thereof, or the salt of the azo compound or the tautomer according to any one of the first to eighth aspects.

A tenth aspect of the present invention provides the aqueous ink composition according to the ninth aspect, further containing a water-soluble organic solvent.

An eleventh aspect of the present invention provides an inkjet recording method including using the ink composition according to the ninth or tenth aspect as an ink, discharging ink droplets of the ink according to the recording signals, and thereby performing recording on a record-receiving material.

A twelfth aspect of the present invention provides the inkjet recording method according to the eleventh aspect, where the record-receiving material is a communication sheet.

A thirteenth aspect of the present invention provides the inkjet recording method according to the twelfth aspect, where the communication sheet is a sheet having an ink-receiving layer containing a porous white inorganic substance.

A fourteenth aspect of the present invention provides an inkjet printer equipped with a vessel containing the ink composition according to the ninth or tenth aspect.

A fifteenth aspect of the present invention provides a colored body colored with any one of the following:

a) the azo compound, the tautomer thereof, or the salt of the azo compound or the tautomer according to any one of the first to eighth aspects, b) the aqueous ink composition according to the ninth or tenth aspect, or c) the inkjet recording method according to the eleventh aspect.

Effects of the Invention

The azo compound of the present invention, the tautomer thereof, or the salt of the azo compound or the tautomer, and an ink composition containing this have high storage stability, and can be suitably used as an ink for inkjet recording. Furthermore, when recording is performed on a paper for inkjet exclusive use, the ink composition exhibits high print density, low color-rendering properties and low color saturation, and has a high-quality black hue. The ink composition has particularly excellent (ozone) gas resistance. Therefore, an ink composition containing the azo compound of the present invention, the tautomer thereof, or the salt of the azo compound or the tautomer is highly useful as a black ink for inkjet recording.

BRIEF DESCRIPTION OF THE DRAWINGS

Hereinafter, the present invention will be described in detail.

For convenience, in the present specification the "azo compound of the present invention, the tautomer thereof, or the salt of the azo compound or the tautomer" will be collectively described briefly as the "azo compound of the present invention" in the following descriptions.

The azo compound of the present invention represented by formula (1) has tautomers, and examples that may be contemplated as these tautomers include compounds of the following formulas (3) and (4), in addition to the compound represented by the formula (1). These compounds are also included in the present invention. Meanwhile, in the formulas (3) and (4), $R^1$ to $R^{13}$ respectively have the same meanings as defined in the formula (1).

examples thereof include 3-sulfophenyl, 4-sulfophenyl, 2,4-disulfophenyl, and 3,5-disulfophenyl. Preferred specific examples include 4-sulfophenyl.

Preferred examples of $R^1$ include a (C1-C4) alkyl group, a (C1-C4) alkyl group substituted with a carboxy group, a phenyl group, and a phenyl group substituted with a sulfo group. More preferred examples include a (C1-C4) alkyl group, a phenyl group, and a phenyl group substituted with a sulfo group.

Even more preferred examples include a (C1-C4) alkyl group and a phenyl group.

Particularly preferred examples include a (C1-C4) alkyl group, and among others, methyl is most preferred.

In the formula (1), $R^2$ represents a cyano group; a carbamoyl group; or a carboxy group. Among these, the cyano group and the carbamoyl group are preferred, and the cyano group is more preferred.

In the formula (1), examples of the (C1-C4) alkyl group for $R^3$ and $R^4$ include the same groups as those mentioned with regard to the (C1-C4) alkyl group for $R^1$, including preferred examples of the group.

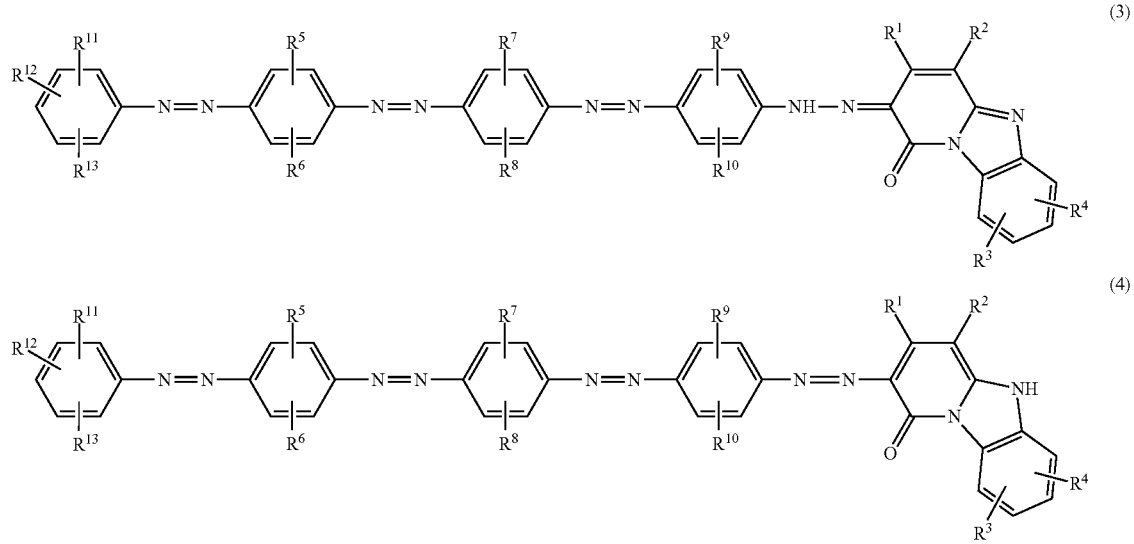

In the formula (1), the (C1-C4) alkyl group for $R^1$ may be an unsubstituted, linear, or branched alkyl group, and a linear alkyl group is preferred. Specific examples thereof include linear groups such as methyl, ethyl, n-propyl, and n-butyl; and branched groups such as isopropyl, isobutyl, sec-butyl, and tert-butyl. Preferred specific examples include methyl and n-propyl, and methyl is particularly preferred.

The (C1-C4) alkyl group substituted with a carboxy group for $R^1$ may be an unsubstituted (C1-C4) alkyl described above having any of the carbon atoms substituted by a carboxy group. There are no particular limitations on the substitution position of the carboxy group, but it is preferable that the carboxy group be substituted at an end of the alkyl group, and that the substitution number of the carboxy group be 1 or 2, and preferably 1. Specific examples thereof include carboxymethyl and 2-carboxyethyl. Preferred specific examples include carboxymethyl.

The phenyl group substituted with a sulfo group for $R^1$ may be a phenyl group substituted with one to three, preferably one or two, sulfo groups, and there are no particular limitations on the substitution position of the sulfo group. Specific The halogen atom for $R^3$ and $R^4$ may be a fluorine atom, a chlorine atom, a bromine atom, or an iodine atom, and a chlorine atom is preferred.

The (C1-C4) alkoxy group for $R^3$ and $R^4$ may be an unsubstituted, linear, or branched alkoxy group, and a linear alkoxy group is preferred. Specific examples thereof include linear groups such as methoxy, ethoxy, n-propoxy, and n-butoxy; and branched groups such as isopropoxy, isobutoxy, sec-butoxy, and tert-butoxy. Among these, methoxy is particularly preferred.

$R^3$ and $R^4$ are each independently preferably a hydrogen atom, a (C1-C4) alkyl group, a (C1-C4) alkoxy group, or a sulfo group.

More preferred is a combination in which any one of them is a hydrogen atom and the other is a sulfo group.

There are no particular limitations on the substitution positions of $R^3$ and $R^4$; however, it is preferable that when any one of them is a hydrogen atom and the other is a sulfo group, the sulfo group be substituted at any of the two carbon atoms that constitute the benzimidazolopyridone ring but that are not adjacent to any of the nitrogen atoms.

In regard to the compound represented by the formula (1) of the present invention, from the viewpoints of ease of synthesis and cheapness, the compound may be used as a mixture including at least two kinds of regioisomers in connection with the substitution positions of $R^3$ and $R^4$.

A preferred example of the combination of $R^1$ to $R^4$ in the formula (1) may be a combination in which $R^1$ is a (C1-C4) alkyl group or a phenyl group (preferably a (C1-C4) alkyl group, and more preferably a methyl group); $R^2$ is a cyano group or a carbamoyl group (preferably a cyano group); $R^3$ is a hydrogen atom, a methyl group, or a methoxy group (preferably a methoxy group); and $R^4$ is a sulfo group.

In the formula (1), the (C1-C4) alkylthio group for $R^5$ may be an unsubstituted alkylthio group with a linear or branched alkyl moiety, and a linear alkyl moiety is preferred. Specific examples thereof include linear groups such as methylthio, ethylthio, n-propylthio, and n-butylthio; and branched groups such as isopropylthio, isobutylthio, sec-butylthio, and tert-butylthio.

The (C1-C4) alkylthio group substituted with at least one kind of group selected from the group consisting of a hydroxy group, a sulfo group, and a carboxy group, which is for $R^5$, may be a (C1-C4) alkylthio group having these substituents on any of the carbon atoms. The number of the relevant substituents is usually 1 or 2, and preferably 1. There are no particular limitations on the position of the substituent, but it is preferable to substitute a carbon atom other than the carbon atom to which the sulfur atom in the alkylthio group is bonded.

Specific examples thereof include hydroxy-(C1-C4) alkylthio groups such as 2-hydroxyethylthio, 2-hydroxypropylthio, and 3-hydroxypropylthio; sulfo-(C1-C4) alkylthio groups such as 2-sulfoethylthio and 3-sulfopropylthio; and carboxy-(C1-C4) alkylthio groups such as 2-carboxyethylthio, 3-carboxypropylthio, and 4-carboxybutylthio.

Among those described above, $R^5$ is preferably a sulfo-(C1-C4) alkylthio group or a carboxy-(C1-C4) alkylthio group, and $R^5$ is more preferably a sulfo-(C1-C4) alkylthio group, and particularly preferably a sulfopropylthio group.

In the formula (1), the (C1-C4) alkylcarbonylamino group for $R^6$ may be an unsubstituted alkylcarbonylamino group having a linear or branched alkyl moiety, and a linear alkyl moiety is preferred. Specific examples thereof include linear groups such as acetylamino (methylcarbonylamino), propionylamino (ethylcarbonylamino), n-propylcarbonylamino, and n-butylcarbonylamino; and branched groups such as isopropylcarbonylamino, isobutylcarbonylamino, sec-butylcarbonylamino, and pivaloylamino (tert-butylcarbonylamino). Among these, linear groups are preferred, and an acetylamino group is particularly preferred.

A preferred combination of $R^5$ and $R^6$ is a combination in which $R^5$ is a sulfo-(C1-C4) alkylthio group and $R^6$ is an acetylamino group, and a combination in which $R^5$ is a sulfopropylthio group and $R^6$ is an acetylamino group is particularly preferred.

In the formula (1), the (C1-C4) alkylthio group for $R^7$ may be an unsubstituted alkylthio group with a linear or branched alkyl moiety, and a linear alkyl moiety is preferred. Specific examples thereof include linear groups such as methylthio, ethylthio, n-propylthio, and n-butylthio; and branched groups such as isopropylthio, isobutylthio, sec-butylthio, and tert-butylthio.

The (C1-C4) alkylthio group substituted with at least one kind of group selected from the group consisting of a hydroxy group, a sulfo group, and a carboxy group, which is for $R^7$, may be a (C1-C4) alkylthio group having these substituents on any of the carbon atoms. The number of the relevant substituents is usually 1 or 2, and preferably 1. There are no particular limitations on the position of the substituent, but it is preferable to have a substituent on a carbon atom other than the carbon atom to which the sulfur atom in the alkylthio group is bonded.

Specific examples thereof include hydroxy-(C1-C4) alkylthio groups such as 2-hydroxyethylthio, 2-hydroxypropylthio, and 3-hydroxypropylthio; sulfo-(C1-C4) alkylthio groups such as 2-sulfoethylthio and 3-sulfopropylthio; and carboxy-(C1-C4) alkylthio groups such as 2-carboxyethylthio, 3-carboxypropylthio, and 4-carboxybutylthio.

Among those described above, $R^7$ is preferably a sulfo-(C1-C4) alkylthio group or a carboxy-(C1-C4) alkylthio group, and a sulfo-(C1-C4) alkylthio group is more preferred, while a sulfopropylthio group is particularly preferred.

In the formula (1), the (C1-C4) alkylcarbonylamino group for $R^8$ may be an unsubstituted alkylcarbonylamino group with a linear or branched alkyl moiety, and a linear alkyl moiety is preferred. Specific examples thereof include linear groups such as acetylamino (methylcarbonylamino), propionylamino (ethylcarbonylamino), n-propylcarbonylamino, and n-butylcarbonylamino; and branched groups such as isopropylcarbonylamino, isobutylcarbonylamino, sec-butylcarbonylamino, and pivaloylamino (tert-butylcarbonylamino). Among these, linear groups are preferred, and an acetylamino group is particularly preferred.

A preferred combination of $R^7$ and $R^8$ is a combination in which $R^7$ is a sulfo-(C1-C4) alkylthio group and $R^8$ is an acetylamino group, and a combination in which $R^7$ is a sulfopropylthio group and $R^8$ is an acetylamino group is particularly preferred.

In the formula (1), examples of the (C1-C4) alkyl group for $R^9$ and $R^{43}$ include the same groups as those mentioned with regard to the (C1-C4) alkyl group for $R^1$, including preferred examples of the group.

Examples of the (C1-C4) alkoxy group for $R^9$ and $R^{10}$ include the same groups as those mentioned with regard to the (C1-C4) alkoxy group for $R^3$ and $R^4$, including preferred examples of the group.

The (C1-C4) alkoxy group substituted with at least one kind of group selected from the group consisting of a hydroxy group, a (C1-C4) alkoxy group, a sulfo group, and a carboxy group, which is for $R^9$ and $R^{10}$, may be a (C1-C4) alkoxy group having these substituents on any of the carbon atoms. The number of the relevant substituents is usually 1 or 2, and preferably 1. There are no particular limitations on the position of the substituents, but it is preferable to have a substituent on a carbon atom other than the carbon atom to which the oxygen atom in the alkoxy group is bonded.

Specific examples thereof include hydroxy-(C1-C4) alkoxy groups such as 2-hydroxyethoxy, 2-hydroxypropoxy, and 3-hydroxypropoxy; sulfo-(C1-C4) alkoxy groups such as 2-sulfoethoxy, 3-sulfopropoxy, and 4-sulfobutoxy; and carboxy-(C1-C4) alkoxy groups such as 2-carboxyethoxy, 3-carboxypropoxy, and 4-carboxybutoxy.

Among those described above, preferred examples of $R^9$ include a sulfo-(C1-C4) alkoxy group and a carboxy-(C1-C4) alkoxy group, and a sulfo-(C1-C4) alkoxy group is more preferred, while a sulfopropoxy group and a sulfobutoxy group are particularly preferred.

Among those described above, preferred examples $R^{10}$ include a (C1-C4) alkyl group, a (C1-C4) alkoxy group, a sulfo-(C1-C4) alkoxy group, a carboxy-(C1-C4) alkoxy group, and an acetylamino group, and a (C1-C4) alkyl group is more preferred, while a methyl group is particularly preferred.

A preferred combination of $R^9$ and $R^{10}$ is a combination in which $R^9$ is a sulfo-(C1-C4) alkoxy group, and $R^{10}$ is a (C1-C4) alkyl group, and a combination in which $R^9$ is a sulfopropoxy group (in particular, a 3-sulfopropoxy group is preferred) and $R^{10}$ is a methyl group, or a combination in which $R^9$ is a sulfobutoxy group (in particular, a 4-sulfobutoxy group is preferred) and $R^{10}$ is a methyl group, is particularly preferred.

In the formula (1), examples of the (C1-C4) alkyl group for $R^{11}$ to $R^{13}$ include the same groups as those mentioned with regard to the (C1-C4) alkyl group for $R^1$, including preferred examples of the group.

Examples of the (C1-C4) alkoxy group for $R^{11}$ to $R^{13}$ include the same groups as those mentioned with regard to the (C1-C4) alkoxy group for $R^3$ and $R^4$, including preferred examples of the group.

Examples of the (C1-C4) alkoxy group substituted with at least one kind of group selected from the group consisting of a hydroxy group, a (C1-C4) alkoxy group, a sulfo group and a carboxy group, which is for $R^{11}$ to $R^{13}$, include the same groups as those mentioned with regard to the (C1-C4) alkoxy group substituted with at least one kind of group selected from the group consisting of a hydroxy group, a (C1-C4) alkoxy group, a sulfo group and a carboxy group, which is for $R^5$ and $R^6$, including preferred examples of the group.

The (C1-C4) alkylsulfonyl group for $R^{11}$ to $R^{13}$ may be a linear or branched alkylsulfonyl group, and a linear group is preferred. Specific examples thereof include linear groups such as methylsulfonyl, ethylsulfonyl, n-propylsulfonyl, and n-butylsulfonyl; and branched groups such as isopropylsulfonyl and isobutylsulfonyl.

Among the groups described above, methylsulfonyl, ethylsulfonyl, and isopropylsulfonyl are preferred, and methylsulfonyl is particularly preferred.

The (C1-C4) alkylsulfonyl group substituted with at least one kind of group selected from the group consisting of a hydroxy group, a sulfo group, and a carboxy group, which is for $R^{11}$ to $R^{13}$, may be a (C1-C4) alkylsulfonyl group having the aforementioned groups substituted on any of the carbon atoms, and the number of the relevant substituents is usually 1 or 2, and preferably 1. There are no particular limitations on the position of substituents.

Specific examples thereof include hydroxy-substituted groups such as hydroxyethylsulfonyl and 2-hydroxypropylsulfonyl; sulfo-substituted groups such as 2-sulfoethylsulfonyl and 3-sulfopropylsulfonyl; and carboxy-substituted groups such as 2-carboxyethylsulfonyl and 3-carboxypropylsulfonyl.

Among those described above, preferred examples of $R^{11}$ include a hydrogen atom, a carboxy group, a sulfo group, a nitro group, a chlorine atom, a methyl group, a methoxy group, and a (C1-C4) alkylsulfonyl group. A hydrogen atom; a carboxy group, a sulfo group, a nitro group, a chlorine atom, or a (C1-C4) alkylsulfonyl, which are all electron-withdrawing substituents; a methyl group; or a methoxy group is more preferred, and a hydrogen atom and a chlorine atom are particularly preferred.

Among those described above, preferred examples of $R^{12}$ include a hydrogen atom, a carboxy group, a sulfo group, a nitro group, a chlorine atom, a methyl group, a methoxy group, a sulfamoyl group, a (C1-C4) alkylsulfonyl group, a carboxy-(C1-C4) alkylsulfonyl group, and a sulfo-(C1-C4) alkylsulfonyl group. A hydrogen atom; a carboxy group, a sulfo group, a nitro group, a chlorine atom, a sulfamoyl group, a (C1-C4) alkylsulfonyl group, a carboxy-(C1-C4)alkylsulfonyl group, or a sulfo-(C1-C4) alkylsulfonyl group, which are all electron-withdrawing substituents; a methyl group; or a methoxy group is preferred, and a sulfo group, a nitro group, a methyl group, a methoxy group, a sulfamoyl group, a sulfopropylsulfonyl group, and a carboxyethylsulfonyl group are more preferred, while a sulfo group is particularly preferred.

Among those described above, preferred examples of $R^{13}$ include a hydrogen atom, a carboxy group, a sulfo group, a methoxy group, a nitro group, a chlorine atom, and a (C1-C4) alkylsulfonyl group. A hydrogen atom; a carboxy group, a sulfo group, a nitro group, a chlorine atom, or a (C1-C4) alkylsulfonyl group, which are all electron-withdrawing groups; or a methoxy group is preferred, and a hydrogen atom is particularly preferred.

A preferred combination of $R^{11}$ to $R^{13}$ is a combination in which $R^{11}$ is a hydrogen atom, $R^{12}$ is a sulfo group, and $R^{13}$ is a hydrogen atom; a combination in which $R^{11}$ is a hydrogen atom, $R^{12}$ is a sulfamoyl group, and $R^{13}$ is a hydrogen atom; or a combination in which $R^{11}$ is a hydrogen atom, $R^{12}$ is a chlorine atom, and $R^{13}$ is a sulfo group. A combination in which $R^{11}$ is a hydrogen atom, $R^{12}$ is a chlorine atom, and $R^{13}$ is a sulfo group, is particularly preferred.

In regard to the various substituents in the formula (1), combinations thereof, substitution positions thereof, and the like, a compound in which preferred kinds thereof previously described are combined is more preferred, and a compound in which more preferred kinds are combined is even more preferred. The same also applies to a combination of more preferred kinds with more preferred kinds, or a combination of preferred kinds with more preferred kinds.

A more preferred compound of the formula (1) is a compound represented by the formula (2) described above.

In the formula (2), $R^1$ to $R^{10}$ have the same meanings as $R^1$ to $R^{10}$ in the formula (1), respectively, and preferred groups and combinations of preferred groups are also the same as those defined in the formula (1). However, it is more preferable that $R^5$ to $R^{10}$ be substituted at the positions of the formula (2).

$R^{11}$ to $R^{13}$ in the formula (2) have the same meanings as $R^{11}$ to $R^{13}$ in the formula (1), and preferred groups and combinations of preferred groups are also the same as those defined in the formula (1).

In the formula (2), more preferred $R^{11}$ to $R^{13}$ can have the substitution positions characterized.

That is, in the benzene ring substituted with $R^{11}$ to $R^{13}$, when the substitution position of the azo group is set to the 1-position, it is preferable that $R^{11}$ be substituted at the 2-position or the 3-position, $R^{12}$ be substituted at the 4-position, and $R^{13}$ be substituted at the 5-position or the 6-position.

It is particularly preferred in regard to the formula (2) that the substitution positions of $R^5$ to $R^{13}$ be characterized as described above, and the types of the substituents may be the same as those defined in the formula (1).

In regard to the formulas (1) and (2), specific examples of preferred combinations include combinations of the following items (i) to (iii). Item (ii) is more preferred than item (i), and item (iii) is most preferred.

(i) A combination in which:
$R^1$ represents a methyl group; or a phenyl group;
$R^2$ represents a cyano group; or a carbamoyl group;
$R^3$ represents a hydrogen atom; a methyl group; or a methoxy group;
$R^4$ represents a sulfo group;
$R^5$ represents a (C1-C4) alkylthio group substituted with a sulfo group or a carboxy group;
$R^6$ represents a (C1-C4) alkylcarbonylamino group;
$R^7$ represents a (C1-C4) alkylthio group substituted with a sulfo group or a carboxy group;
$R^8$ represents a (C1-C4) alkylcarbonylamino group;
$R^9$ represents a sulfo-(C1-C4) alkoxy group;
$R^{10}$ represents a (C1-C4) alkyl group; or an acetylamino group; and $R^{11}$ to $R^{13}$ each independently represent a hydrogen atom; a carboxy group; a sulfo group; a chlorine atom; a nitro group; a methyl group; a methoxy group; a sulfamoyl group; or a (C1-C4) alkylsulfonyl group substituted with a sulfo group or a carboxy group.

(ii) A combination in which:
$R^1$ represents a methyl group;
$R^2$ represents a cyano group; a methyl group; or a methoxy group;
$R^3$ represents a hydrogen atom; a methyl group; or a methoxy group;
$R^4$ represents a sulfo group;
$R^5$ represents a sulfo-(C1-C4) alkylthio group;
$R^6$ represents a (C1-C4) alkylcarbonylamino group;
$R^7$ represents a sulfo-(C1-C4) alkylthio group;
$R^8$ represents a (C1-C4) alkylcarbonylamino group;
$R^9$ represents a sulfo-(C1-C4) alkoxy group;
$R^{10}$ represents a (C1-C4) alkyl group; or an acetylamino group; and
$R^{11}$ to $R^{13}$ each independently represent a hydrogen atom; a carboxy group; a sulfo group; a chlorine atom; a nitro group; a methyl group; a methoxy group; or a sulfamoyl group;

(iii) A combination in which:
$R^1$ represents a methyl group;
$R^2$ represents a cyano group;
$R^3$ represents a hydrogen atom; or a methoxy group;
$R^4$ represents a sulfo group;
$R^5$ represents a sulfo-(C1-C4) alkylthio group;
$R^6$ represents an acetylamino group;
$R^7$ represents a sulfo-(C1-C4) alkylthio group;
$R^8$ represents an acetylamino group;
$R^9$ represents a sulfopropoxy group; or a sulfobutoxy group;
$R^{10}$ represents a (C1-C4) alkyl group;
$R^{11}$ represents a hydrogen atom; or a sulfo group;
$R^{12}$ represents a sulfo group; or a chlorine atom; and
$R^{13}$ represents a hydrogen atom; or a sulfo group.

The azo compound of the present invention represented by the formula (1) can be synthesized, for example, by the following method. Furthermore, the structural formulas of the compounds in the various processes will be presented in the form of free acid.

Meanwhile, in the following formulas (5) to (12), $R^1$ to $R^{13}$ respectively have the same meanings as defined in the formula (1).

A compound represented by the following formula (5) is diazotized by a conventional method, the diazo compound thus obtained and a compound represented by the following formula (6) are subjected to a coupling reaction by a conventional method, and thereby a compound represented by the following formula (7) is obtained.

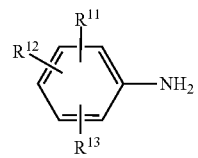
(5)

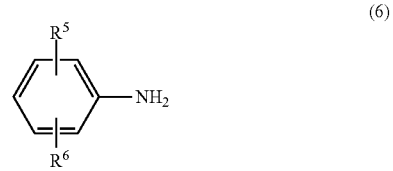
(6)

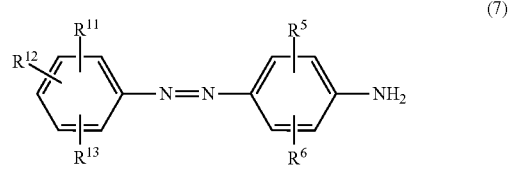
(7)

The compound represented by the formula (7) and thus obtained is diazotized by a conventional method, subsequently the diazo compound thus obtained and the compound represented by the following formula (8) are subjected to a coupling reaction by a conventional method, and thereby a compound represented by the following formula (9) is obtained.

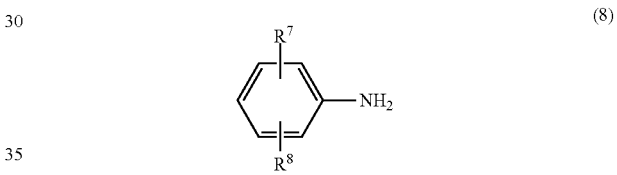
(8)

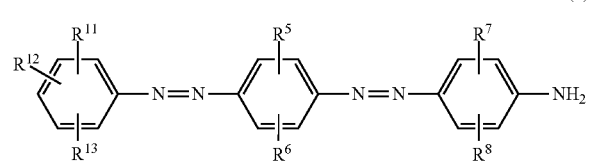
(9)

The compound represented by the formula (9) and thus obtained is diazotized by a conventional method, subsequently the diazo compound thus obtained and a compound represented by the following formula (10) are subjected to a coupling reaction by a conventional method, and thereby the compound represented by the following formula (11) is obtained.

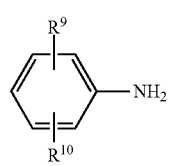
(10)

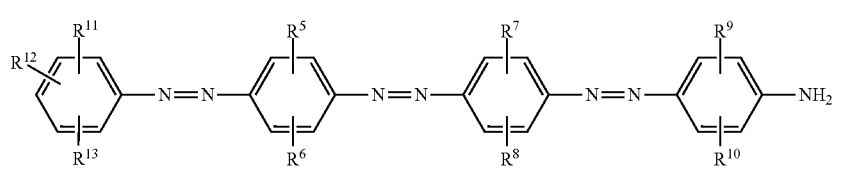
(11)

The compound represented by the formula (11) and thus obtained is diazotized by a conventional method, subsequently the diazo compound thus obtained and a compound represented by the following formula (12) are subjected to a coupling reaction by a conventional method, and thereby the azo compound of the present invention represented by the formula (1) can be obtained.

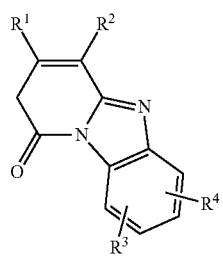

(12)

In addition, the compound represented by the formula (12) can be synthesized according to the method described in Patent Document 3.

There are no particular limitations on suitable specific examples of the azo compound of the present invention represented by the formula (1), but suitable specific examples thereof include compounds represented by the structural formulas listed in the following Tables 1 to 16.

In each table, functional groups such as a sulfo group and a carboxy group will be described, for convenience, in the form of free acid.

TABLE 1

| Compound No. | Structural formula |
| --- | --- |
| 1 | |
| 2 | |
| 3 | |

TABLE 1-continued

| Compound No. | Structural formula |
| --- | --- |
| 4 | (structure) |
| 5 | (structure) |
| 6 | (structure) |

TABLE 2

| Compound No. | Structural formula |
| --- | --- |
| 7 | (structure) |

TABLE 2-continued

| Compound No. | Structural formula |
|---|---|
| 8 | |
| 9 | |
| 10 | |
| 11 | |

TABLE 2-continued
| Compound No. | Structural formula |
|---|---|
| 12 | 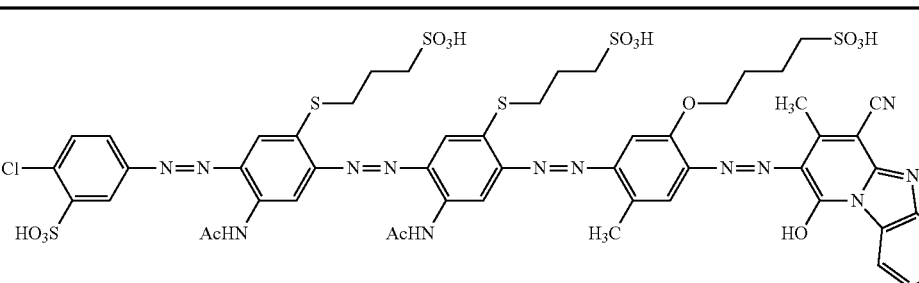 |
TABLE 3
| Compound No. | Structural formula |
|---|---|
| 13 | 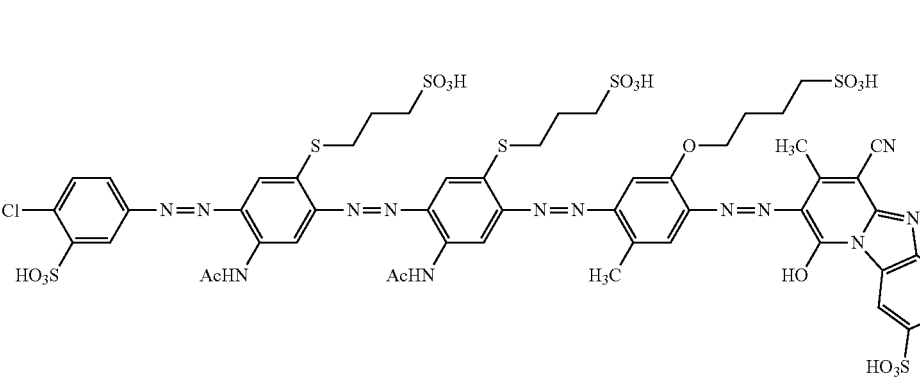 |
| 14 | |
| 15 | 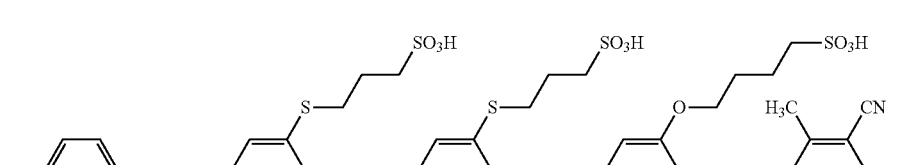 |

TABLE 3-continued

| Compound No. | Structural formula |
| --- | --- |
| 16 | (structure) |
| 17 | (structure) |
| 18 | (structure) |

TABLE 4

| Compound No. | Structural formula |
| --- | --- |
| 19 | (structure) |

TABLE 4-continued
| Compound No. | Structural formula |
|---|---|
| 20 | 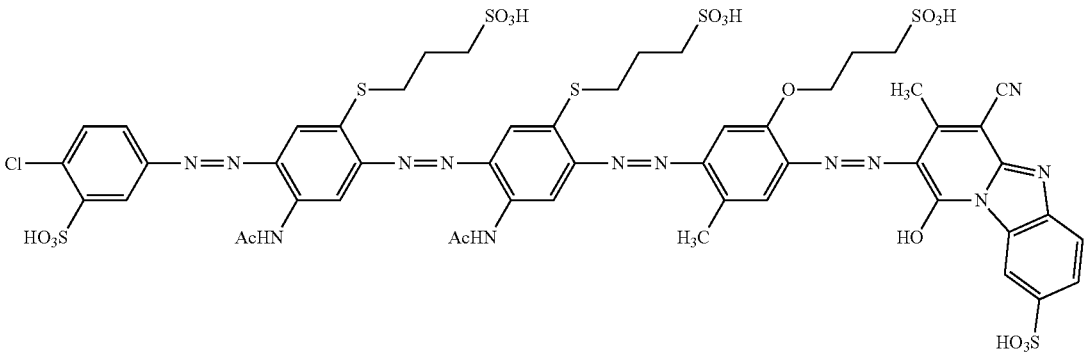 [SMILES: CC(=O)Nc1cc(N=Nc2cc(SCCCS(=O)(=O)O)c(N=Nc3cc(OCCCCS(=O)(=O)O)c(N=Nc4c(C)c(C#N)c5nc6ccc(S(=O)(=O)O)cc6n5c4O)cc3C)cc2NC(C)=O)c(SCCCS(=O)(=O)O)cc1N=Nc1ccc(Cl)c(S(=O)(=O)O)c1] |
| 21 | 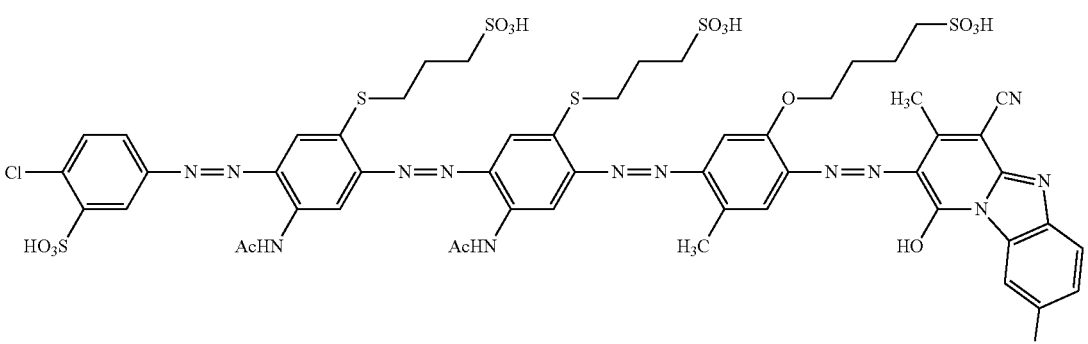 |
| 22 | 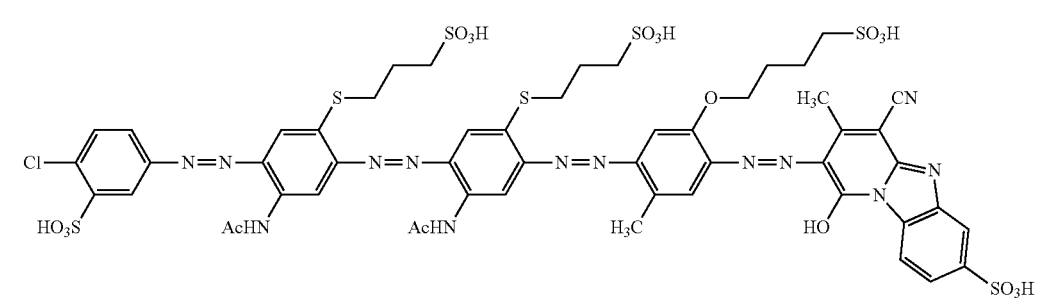 [SMILES: CC(=O)Nc1cc(N=Nc2cc(SCCCS(=O)(=O)O)c(N=Nc3cc(OCCCCS(=O)(=O)O)c(N=Nc4c(C)c(C#N)c5nc6cc(S(=O)(=O)O)ccc6n5c4O)cc3C)cc2NC(C)=O)c(SCCCS(=O)(=O)O)cc1N=Nc1ccc(Cl)c(S(=O)(=O)O)c1] |
| 23 | 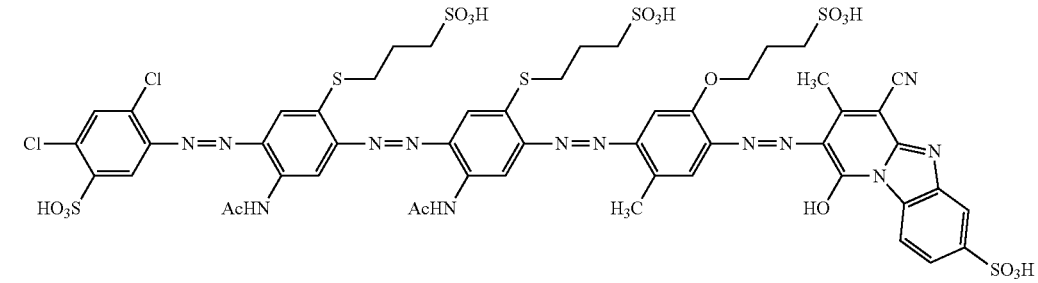 [SMILES: CC(=O)Nc1cc(N=Nc2cc(SCCCS(=O)(=O)O)c(N=Nc3cc(OCCCS(=O)(=O)O)c(N=Nc4c(C)c(C#N)c5nc6cc(S(=O)(=O)O)ccc6n5c4O)cc3C)cc2NC(C)=O)c(SCCCS(=O)(=O)O)cc1N=Nc1cc(S(=O)(=O)O)c(Cl)cc1Cl] |

TABLE 4-continued
| Compound No. | Structural formula |
| --- | --- |
| 24 | 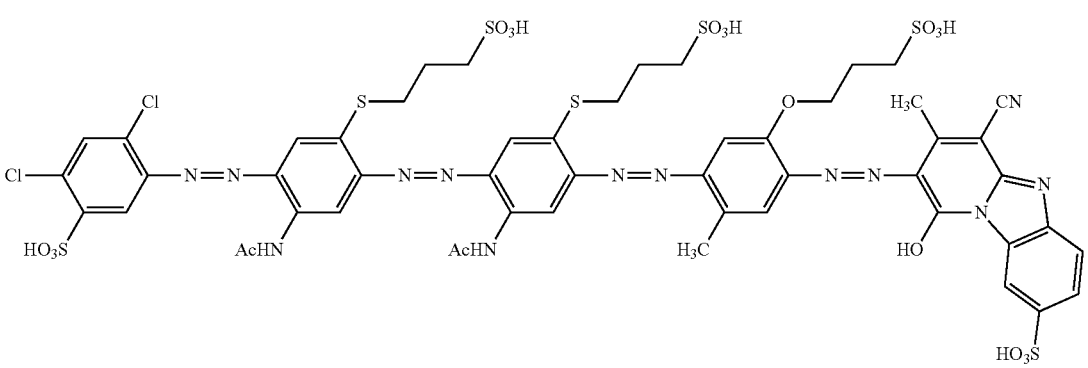 [SMILES: CC(=O)Nc1cc(N=Nc2cc(SCCCS(=O)(=O)O)c(N=Nc3cc(OCCCS(=O)(=O)O)c(N=Nc4c(C)c(C#N)c5nc6ccc(S(=O)(=O)O)cc6n5c4O)cc3C)cc2NC(C)=O)c(SCCCS(=O)(=O)O)cc1N=Nc1cc(S(=O)(=O)O)c(Cl)cc1Cl] |
TABLE 5
| Compound No. | Structural formula |
| --- | --- |
| 25 | 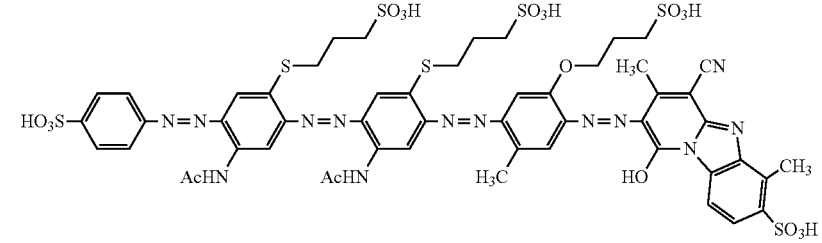 [SMILES: CC(=O)Nc1cc(N=Nc2cc(SCCCS(=O)(=O)O)c(N=Nc3cc(OCCCS(=O)(=O)O)c(N=Nc4c(C)c(C#N)c5nc6c(C)c(S(=O)(=O)O)ccc6n5c4O)cc3C)cc2NC(C)=O)c(SCCCS(=O)(=O)O)cc1N=Nc1ccc(S(=O)(=O)O)cc1] |
| 26 | 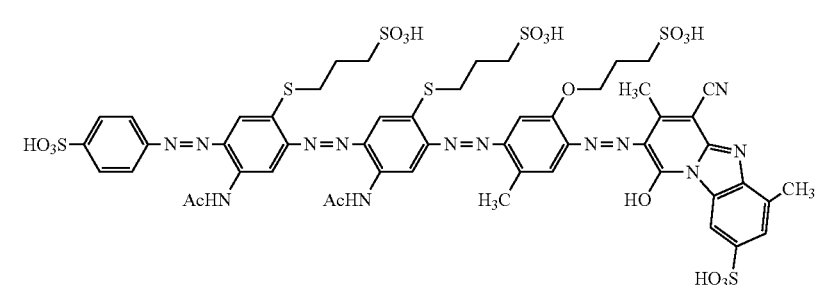 [SMILES: CC(=O)Nc1cc(N=Nc2cc(SCCCS(=O)(=O)O)c(N=Nc3cc(OCCCS(=O)(=O)O)c(N=Nc4c(C)c(C#N)c5nc6c(C)cc(S(=O)(=O)O)cc6n5c4O)cc3C)cc2NC(C)=O)c(SCCCS(=O)(=O)O)cc1N=Nc1ccc(S(=O)(=O)O)cc1] |
| 27 | 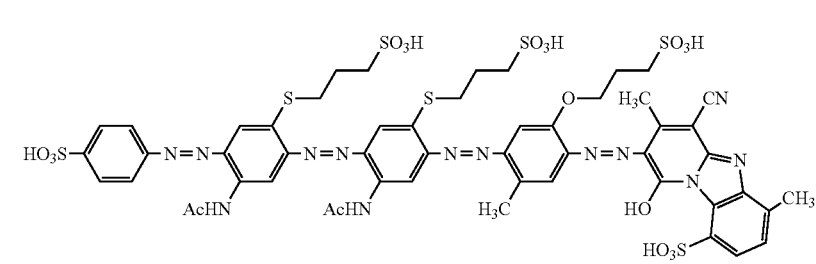 [SMILES: CC(=O)Nc1cc(N=Nc2cc(SCCCS(=O)(=O)O)c(N=Nc3cc(OCCCS(=O)(=O)O)c(N=Nc4c(C)c(C#N)c5nc6c(C)ccc(S(=O)(=O)O)c6n5c4O)cc3C)cc2NC(C)=O)c(SCCCS(=O)(=O)O)cc1N=Nc1ccc(S(=O)(=O)O)cc1] |

TABLE 5-continued

| Compound No. | Structural formula |
|---|---|
| 28 | |
| 29 | |
| 30 | |

TABLE 6

| Compound No. | Structural formula |
|---|---|
| 31 | |
| 32 | |

TABLE 6-continued

| Compound No. | Structural formula |
|---|---|
| 33 | (structure) |
| 34 | (structure) |
| 35 | (structure) |
| 36 | (structure) |

TABLE 7

| Compound No. | Structural formula |
|---|---|
| 37 | (structure) |

TABLE 7-continued

| Compound No. | Structural formula |
| --- | --- |
| 38 | (structure) |
| 39 | (structure) |
| 40 | (structure) |
| 41 | (structure) |
| 42 | (structure) |

TABLE 8

| Compound No. | Structural formula |
|---|---|
| 43 | |
| 44 | |
| 45 | |
| 46 | |
| 47 | |

TABLE 8-continued

| Compound No. | Structural formula |
|---|---|
| 48 | (structure) |

TABLE 9

| Compound No. | Structural formula |
|---|---|
| 49 | (structure) |
| 50 | (structure) |
| 51 | (structure) |
| 52 | (structure) |

TABLE 9-continued

| Compound No. | Structural formula |
|---|---|
| 53 | (structure) |
| 54 | (structure) |

TABLE 10

| Compound No. | Structural formula |
|---|---|
| 55 | (structure) |
| 56 | (structure) |
| 57 | (structure) |

TABLE 10-continued

| Compound No. | Structural formula |
|---|---|
| 58 | |
| 59 | |
| 60 | |

TABLE 11

| Compound No. | Structural formula |
|---|---|
| 61 | |
| 62 | |

TABLE 11-continued

| Compound No. | Structural formula |
|---|---|
| 63 | (structure) |
| 64 | (structure) |
| 65 | (structure) |
| 66 | (structure) |

TABLE 12

| Compound No. | Structural formula |
|---|---|
| 67 | (structure) |

TABLE 12-continued
| Compound No. | Structural formula |
|---|---|
| 68 | 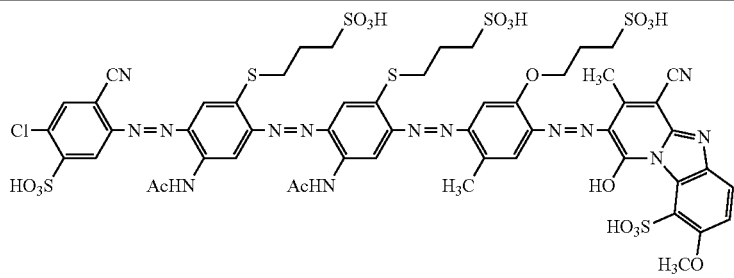 |
| 69 | 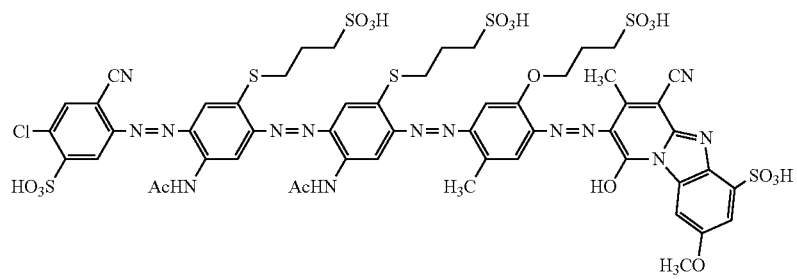 [SMILES: COc1cc(S(=O)(=O)O)c2nc3c(C#N)c(C)c(N=Nc4cc(C)c(N=Nc5cc(NC(C)=O)c(N=Nc6cc(NC(C)=O)c(N=Nc7cc(S(=O)(=O)O)c(Cl)cc7C#N)cc6SCCCS(=O)(=O)O)cc5SCCCS(=O)(=O)O)cc4OCCCS(=O)(=O)O)c(O)n3c2c1] |
| 70 | 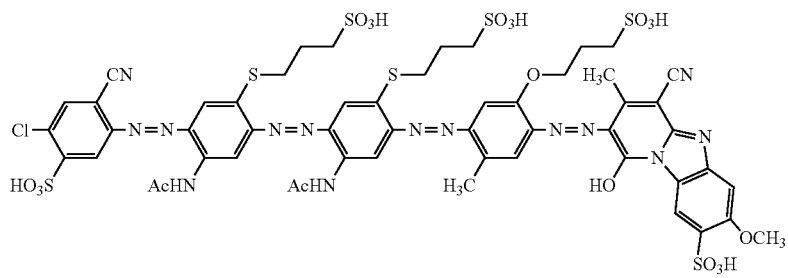 [SMILES: COc1cc2nc3c(C#N)c(C)c(N=Nc4cc(C)c(N=Nc5cc(NC(C)=O)c(N=Nc6cc(NC(C)=O)c(N=Nc7cc(S(=O)(=O)O)c(Cl)cc7C#N)cc6SCCCS(=O)(=O)O)cc5SCCCS(=O)(=O)O)cc4OCCCS(=O)(=O)O)c(O)n3c2cc1S(=O)(=O)O] |
| 71 | 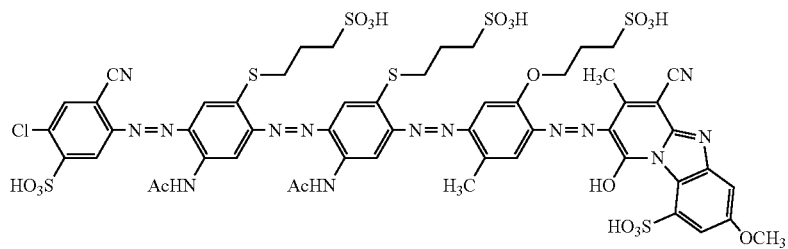 [SMILES: COc1cc(S(=O)(=O)O)c2c(c1)nc1c(C#N)c(C)c(N=Nc3cc(C)c(N=Nc4cc(NC(C)=O)c(N=Nc5cc(NC(C)=O)c(N=Nc6cc(S(=O)(=O)O)c(Cl)cc6C#N)cc5SCCCS(=O)(=O)O)cc4SCCCS(=O)(=O)O)cc3OCCCS(=O)(=O)O)c(O)n12] |
| 72 | 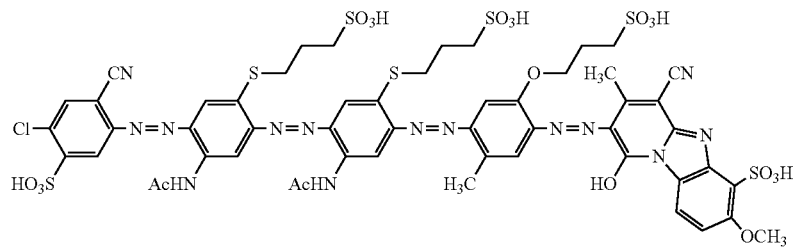 [SMILES: COc1ccc2c(nc3c(C#N)c(C)c(N=Nc4cc(C)c(N=Nc5cc(NC(C)=O)c(N=Nc6cc(NC(C)=O)c(N=Nc7cc(S(=O)(=O)O)c(Cl)cc7C#N)cc6SCCCS(=O)(=O)O)cc5SCCCS(=O)(=O)O)cc4OCCCS(=O)(=O)O)c(O)n32)c1S(=O)(=O)O] |

TABLE 13

| Compound No. | Structural formula |
|---|---|
| 73 | (structure) |
| 74 | (structure) |
| 75 | (structure) |
| 76 | (structure) |
| 77 | (structure) |
| 78 | (structure) |

TABLE 14

| Compound No. | Structural formula |
|---|---|
| 79 | |
| 80 | |
| 81 | |
| 82 | |
| 83 | |

TABLE 14-continued

| Compound No. | Structural formula |
|---|---|
| 84 | (structure) |

TABLE 15

| Compound No. | Structural formula |
|---|---|
| 85 | (structure) |
| 86 | (structure) |
| 87 | (structure) |
| 88 | (structure) |

TABLE 15-continued

| Compound No. | Structural formula |
|---|---|
| 89 | (structure) |
| 90 | (structure) |

TABLE 16

| Compound No. | Structural formula |
|---|---|
| 91 | (structure) |
| 92 | (structure) |
| 93 | (structure) |

TABLE 16-continued

| Compound No. | Structural formula |
|---|---|
| 94 | (structure shown) |
| 95 | (structure shown) |
| 96 | (structure shown) |

Diazotization of the compound represented by the formula (5) is carried out by a method that is known per se, and is carried out, for example, by using a nitrous acid salt, for example, a nitrous acid alkali-metal salt such as sodium nitrite, in an inorganic acid medium at a temperature of, for example, −5° C. to 30° C., and preferably 0° C. to 15° C.

Coupling of the diazotization product of the compound represented by the formula (5) and the compound represented by the formula (6) is also carried out under conditions that are known per se. It is advantageous to carry out the coupling in water or an aqueous organic medium at a temperature of, for example, −5° C. to 30° C., and preferably 0° C. to 25° C., and at a pH value ranging from acidic to neutral, for example, at pH 1 to 6. Since the diazotization-reaction liquid is acidic and the reaction system becomes further acidified as a result of the progress of the coupling reaction, adjustment of the pH value of the reaction liquid to preferred conditions is carried out by the addition of a base. As the base, for example, an alkali-metal hydroxide such as lithium hydroxide or sodium hydroxide; an alkali-metal carbonate such as lithium carbonate, sodium carbonate, or potassium carbonate; an acetic acid salt such as sodium acetate; ammonia; or an organic amine can be used.

The compound represented by the formula (5) and the compound represented by the formula (6) are used in near-stoichiometric amounts.

Diazotization of the compound represented by the formula (7) is carried out by a method that is known per se, and is carried out, for example, by using a nitrous acid salt, for example, a nitrous acid alkali-metal salt such as sodium nitrite, in an inorganic acid medium at a temperature of, for example, −5° C. to 40° C., and preferably 5° C. to 30° C.

Coupling between the diazotization product of the compound represented by the formula (7) and the compound represented by the formula (8) is also carried out under conditions that are known per se. It is advantageous to carry out the reaction in water or an aqueous organic medium at a temperature of, for example, −5° C. to 40° C., and preferably 10° C. to 30° C., and at a pH value ranging from acidic to neutral, for example, at pH 2 to 7. Since the diazotization reaction liquid is acidic, and the reaction system becomes further acidified by the progress of the coupling reaction, adjustment of the pH value of the reaction liquid to preferred conditions is carried out by the addition of a base. Regarding the base, the same bases as those described above can be used.

The compound represented by the formula (7) and the compound represented by the formula (8) are used in near-stoichiometric amounts.

Diazotization of the compound represented by the formula (9) is carried out by a method that is known per se, and is carried out, for example, by using a nitrous acid salt, for example, a nitrous acid alkali-metal salt such as sodium nitrite in an organic acid medium at a temperature of, for example, −5° C. to 50° C., and preferably 5° C. to 40° C.

Coupling of the diazotization product of the compound represented by the formula (9) and the compound represented by the formula (10) is also carried out under conditions that are known per se. It is advantageous to carry out the reaction in water or an aqueous organic medium at a temperature of, for example, −5° C. to 50° C., and preferably 10° C. to 40° C., and at a pH value ranging from acidic to neutral, for example, at pH 2 to 7. Since the diazotization reaction liquid is acidic, and the reaction system becomes further acidified as the coupling reaction progresses, adjustment of the pH value of the reaction liquid to preferred conditions is carried out by the addition of a base. Regarding the base, the same bases as those described above can be used.

The compound represented by the formula (9) and the compound represented by the formula (10) are used in near-stoichiometric amounts.

Diazotization of the compound represented by the formula (11) is carried out by a method that is known per se, and is carried out, for example, by using a nitrous acid salt, for example, a nitrous acid alkali-metal salt such as sodium nitrite in an organic acid medium at a temperature of, for example, −5° C. to 50° C., and preferably 10° C. to 40° C.

Coupling of the diazotization product of the compound represented by the formula (11) and the compound represented by the formula (12) is also carried out under conditions that are known per se. It is advantageous to carry out the reaction in water or an aqueous organic medium at a temperature of, for example, −5° C. to 50° C., and preferably 10° C. to 40° C., and at a pH value ranging from weakly acidic to alkaline. The reaction is carried out preferably at a pH value ranging from weakly acidic to weakly alkaline, for example, at pH 5 to 10, and adjustment of the pH value is carried out by the addition of a base. Regarding the base, the same bases as those described above can be used.

The compound represented by the formula (11) and the compound represented by the formula (12) are used in near-stoichiometric amounts.

The salt of the azo compound represented by the formula (1) is a salt with an inorganic or organic cation. Among them, examples of the salt with an inorganic cation include an alkali-metal salt, an alkaline-earth metal salt, and an ammonium salt, and preferred inorganic salts include salts of lithium, sodium, and potassium, and ammonium salts. Furthermore, examples of the salt with an organic cation include salts with quaternary ammonium ions represented by the following formula (13), but the relevant salts are not intended to be limited to these.

properties that serve the purpose can be obtained by selecting an appropriate kind of salt as necessary, or in the case where plural salts and the like are included, by changing the ratio of the salts.

(13)

In the formula (13), $Z^1$, $Z^2$, $Z^3$, and $Z^4$ each independently represent a group selected from the group consisting of a hydrogen atom, an unsubstituted alkyl group, a hydroxyalkyl group, and a hydroxyalkoxyalkyl group, and at least one of them is a group other than a hydrogen atom.

Specific examples of the alkyl group for $Z^1$ to $Z^4$ in the formula (13) include methyl, ethyl, n-propyl, isopropyl, n-butyl, isobutyl, sec-butyl, and tert-butyl, and specific examples of the hydroxyalkyl group include hydroxy-(C1-C4) alkyl groups such as hydroxymethyl, hydroxyethyl, 3-hydroxypropyl, 2-hydroxypropyl, 4-hydroxybutyl, 3-hydroxybutyl, and 2-hydroxybutyl. Specific examples of the hydroxyalkoxyalkyl group include hydroxy-(C1-C4) alkoxy-(C1-C4) alkyl groups such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl, and 2-hydroxyethoxybutyl. Among these, a hydroxyethoxy-(C1-C4) alkyl is preferred. Particularly preferred examples include a hydrogen atom; methyl; a hydroxyl-(C1-C4) alkyl group such as hydroxymethyl, hydroxyethyl, 3-hydroxypropyl, 2-hydroxypropyl, 4-hydroxybutyl, 3-hydroxybutyl, or 2-hydroxybutyl; and a hydroxyethoxy-(C1-C4) alkyl group such as hydroxyethoxymethyl, 2-hydroxyethoxyethyl, 3-hydroxyethoxypropyl, 2-hydroxyethoxypropyl, 4-hydroxyethoxybutyl, 3-hydroxyethoxybutyl, or 2-hydroxyethoxybutyl.

Specific examples of the combination of $Z^1$, $Z^2$, $Z^3$, and $Z^4$ in a preferred compound represented by formula (13) will be disclosed in the following Table 17.

TABLE 17

| Compound No. | $Z^1$ | $Z^2$ | $Z^3$ | $Z^4$ |
|---|---|---|---|---|
| 1-1 | H | CH3 | CH3 | CH3 |
| 1-2 | CH3 | CH3 | CH3 | CH3 |
| 1-3 | H | —C2H4OH | —C2H4OH | —C2H4OH |
| 1-4 | CH3 | —C2H4OH | —C2H4OH | —C2H4OH |
| 1-5 | H | —CH2CH(OH)CH3 | —CH2CH(OH)CH3 | —CH2CH(OH)CH3 |
| 1-6 | CH3 | —CH2CH(OH)CH3 | —CH2CH(OH)CH3 | —CH2CH(OH)CH3 |
| 1-7 | H | —C2H4OH | H | —C2H4OH |
| 1-8 | CH3 | —C2H4OH | H | —C2H4OH |
| 1-9 | H | —CH2CH(OH)CH3 | H | —CH2CH(OH)CH3 |
| 1-10 | CH3 | —CH2CH(OH)CH3 | H | —CH2CH(OH)CH3 |
| 1-11 | CH3 | —C2H4OH | CH3 | —C2H4OH |
| 1-12 | CH3 | —CH2CH(OH)CH3 | CH3 | —CH2CH(OH)CH3 |

Furthermore, free acids of the azo compound of the present invention, tautomers thereof, and various salts of the free acids and the tautomers may also be used. For example, any combinations such as a mixture of a sodium salt and an ammonium salt, a mixture of a free acid and a sodium salt, and a mixture of a lithium salt, a sodium salt and an ammonium salt, may also be used. Different kinds of salt may give different property values such as solubility, and a mixture having Examples of the method for synthesizing a desired salt of the azo compound represented by the formula (1) of the present invention include a method of adding a desired inorganic salt or an organic quaternary ammonium salt to the reaction liquid after completion of the final process in the synthesis reaction for the compound represented by the formula (1), and performing salting-out; and a method of isolating the azo compound in a free acid form from the reaction liquid by adding a mineral acid such as hydrochloric acid to the reaction liquid, subsequently washing the free acid thus obtained with water, acidic water, an aqueous organic medium, or the like as necessary, removing impurities such as attached inorganic salts, adding a desired inorganic base or an organic base corresponding to the aforementioned quaternary ammonium salt to the free acid again in an aqueous medium (preferably, in water), and thereby forming a salt. By means of such a method, a desired salt of the azo compound can be obtained in the state of a solution or a precipitated salt. Here, "acidic water" means water acidified by dissolving, for example, a mineral acid such as sulfuric acid or hydrochloric acid, or an organic acid such as acetic acid, in water. Furthermore, the aqueous organic medium means a mixture of water with an organic substance and/or an organic solvent, all of which are miscible with water.

Examples of this organic substance and this organic solvent that are miscible with water include water-soluble organic solvents that will be described below.

Examples of the inorganic salt that is used when the azo compound represented by the formula (1) is converted to a desired salt include halides of alkali metals, such as lithium chloride, sodium chloride, and potassium chloride; carbonates of alkali metals such as lithium carbonate, sodium carbonate, and potassium carbonate; hydroxides of alkali metals, such as lithium hydroxide, sodium hydroxide, and potassium hydroxide; halides of ammonium ion, such as ammonium chloride and ammonium bromide; and hydroxides of ammonium ion, such as ammonium hydroxide (aqueous ammonia).

Furthermore, examples of the salts of organic cations include, for example, halides of the quaternary ammonium ion represented by the formula (13), such as diethanolamine hydrochloride and triethanolamine hydrochloride.

The ink composition of the present invention will be described. The azo compound represented by the formula (1) of the present invention can dye a material formed from cellulose, when formulated into an aqueous composition containing the relevant compound. Furthermore, the azo compound is also capable of dyeing a material having a carbonamide bond, and can be widely used in the dyeing of leather, fabric, paper, and the like. On the other hand, a representative method of using the compound of the present invention may involve an ink composition obtained by dissolving the compound in a liquid medium, and it is preferable to use the compound as an ink composition for inkjet recording.

A reaction liquid containing the compound represented by the formula (1), for example, the reaction liquid obtained after completion of the final process in the synthesis reaction for the compound represented by the formula (1), can be directly used in the preparation of an ink composition. Alternatively, the compound is isolated from the reaction liquid according to a method such as a method of drying, for example, spray drying the reaction liquid; a method of performing salting-out by adding an inorganic salt such as sodium chloride, potassium chloride, calcium chloride, or sodium sulfate to the reaction liquid; a method of performing acid-out by adding a mineral acid such as hydrochloric acid, sulfuric acid, or nitric acid to the reaction liquid; or a method of performing acid-salting-out combining the salting-out process and the acid-out process, and an ink composition can be prepared by using this compound. The azo compound of the present invention is preferably used after being isolated.

The ink composition of the present invention is an aqueous ink composition containing the azo compound represented by the formula (1) of the present invention as a coloring matter, in an amount of usually 0.1% to 20% by mass, preferably 1% to 10% by mass, and more preferably 2% to 8% by mass. The ink composition of the present invention is prepared by using water as a medium, and if necessary, the ink composition may contain a water-soluble organic solvent or an ink preparation agent insofar as the effect of the present invention is not impaired. The water-soluble organic solvent may function as a coloring matter solubilizing agent, a drying-preventing agent (wetting agent), a viscosity-adjusting agent, a penetration enhancer, a surface tension-adjusting agent, a defoamant, or the like, and the water-soluble organic solvent is preferably included in the ink composition of the present invention. Examples of the ink preparation agent include known additives such as a preservative and fungicide, a pH-adjusting agent, a chelating agent, an antirusting agent, a water-soluble ultraviolet absorber, a water-soluble polymer compound, a coloring matter-solubilizing agent, an an antioxidant, and a surfactant. The ink composition of the present invention may contain the water-soluble organic solvent in an amount of 0% to 30% by mass, and preferably 5% to 30% by mass, and the ink preparation agent in an amount of 0% to 15% by mass, and preferably 0% to 7% by mass, all relative to the total mass of the ink composition. The remaining portion excluding the components described above is water. In addition, the pH of the ink composition is preferably pH 5 to 11, and more preferably pH 7 to 10, from the viewpoint of enhancing storage stability. Furthermore, the surface tension of the ink composition is preferably 25 mN/m to 70 mN/m, and more preferably 25 mN/m to 60 mN/m. Also, the viscosity of the ink composition is preferably 30 mPa·s or less, and more preferably 20 mPa·s or less.

The ink composition of the present invention may appropriately contain other coloring matters for color mixing in addition to the azo compound of the present invention, for the purpose of adjusting the subtle tinge of black color. Even in this case, the total mass of the coloring matters included in the ink composition of the present invention may be in the range described above relative to the total mass of the ink composition.

Examples of the coloring matters for color mixing include other coloring matters having various hues such as yellow (for example, C.I. Direct Yellow 34, C.I. Direct Yellow 58, C.I. Direct Yellow 86, C.I. Direct Yellow 132, and C.I. Direct Yellow 161), orange (for example, C.I. Direct Orange 17, C.I. Direct Orange 26, C.I. Direct Orange 29, C.I. Direct Orange 39, and C.I. Direct Orange 49), brown, scarlet (for example, C.I. Direct Red 89), red (for example, C.I. Direct Red 62, C.I. Direct Red 75, C.I. Direct Red 79, C.I. Direct Red 80, C.I. Direct Red 84, C.I. Direct Red 225, and C.I. Direct Red 226), magenta (for example, C.I. Direct Red 227), violet, blue, navy, cyan (for example, C.I. Direct Blue 199 and C.I. Acid Blue 249), green, and black.

The ink composition of the present invention can be used after having one or more kinds of these coloring matters for color mixing incorporated therein, insofar as the effect obtainable by the azo compound of the present invention is not impaired. Even in this case, the total amount of coloring matter that is included in the ink composition may be in the range described above. Furthermore, the mixing ratio of the azo compound of the present invention and the coloring matters for color mixing may depend on the hues of the coloring matters for color mixing, but the mixing ratio is approximately from 20:1 to 1:2, and preferably from 10:1 to 1:1.

When the ink composition of the present invention is used as an ink for inkjet recording, it is preferable to use an ink composition having a reduced content of inorganic impurities such as chlorides and sulfates of metal cations in the azo compound of the present invention. The criterion for the content of inorganic impurities is roughly about 1% by mass or less relative to the total mass of the coloring matters. The lower limit is desirably equal to or less than the detection limit of the analytical instrument, that is, 0%. In order to produce an azo compound of the present invention having a reduced amount of inorganic impurities, for example, a desalination treatment may be carried out by a known method such as a method of using a reverse-osmosis membrane; or a method of performing suspension purification by stirring a dried product or wet cake of the azo compound of the present invention in an alcohol such as methanol, and preferably a mixed solvent of a (C1-C4) alcohol and water, separating precipitate by filtration, and then drying the precipitate.

Specific examples of the water-soluble organic solvent that can be used in the preparation of the ink composition of the present invention include, for example, (C1-C4) alcohols such as methanol, ethanol, propanol, isopropanol, butanol, isobutanol, secondary butanol, and tertiary butanol; carboxylic acid amides such as N,N-dimethylformamide and N,N-dimethylacetamide; lactams such as 2-pyrrolidone, hydroxyethyl-2-pyrrolidone, N-methyl-2-pyrrolidone, and N-methylpyrrolidin-2-one; cyclic ureas such as 1,3-dimethylimidazolidin-2-one and 1,3-dimethylhexahydropyrimid-2-one; ketones or keto-alcohols such as acetone, methyl ethyl ketone, and 2-methyl-2-hydroxypentan-4-one; cyclic ethers such as tetrahydrofuran and dioxane; mono-, oligo-, or poly-alkylene glycols or thioglycols having C2-C6 alkylene units, such as ethylene glycol, 1,2-propylene glycol, 1,3-propylene glycol, 1,2-butylene glycol, 1,4-butylene glycol, 1,6-hexylene glycol, diethylene glycol, triethylene glycol, tetraethylene glycol, dipropylene glycol, polyethylene glycol, polypropylene glycol, thiodiglycol, and dithiodiglycol; polyols (preferably, triols) such as trimethylolpropane, glycerin, and hexane-1,2,6-triol; (C1-C4) alkyl ethers of polyhydric alcohols, such as ethylene glycol monomethyl ether, ethylene glycol monoethyl ether, diethylene glycol monomethyl ether, diethylene glycol monoethyl ether, diethylene glycol monobutyl ether (butyl carbitol), triethylene glycol monomethyl ether, and triethylene glycol monoethyl ether; γ-butyrolactone; dimethyl sulfoxide; and the like. These organic solvents may be used singly, or two or more kinds may be used in combination.

Meanwhile, the water-soluble organic solvents described above include substances that are solid at normal temperature, such as trimethylolpropane; however, since these exhibit water-solubility even when they are solid, and can be used, when dissolved in water, for the same purpose as that of the water-soluble organic solvent, for convenience the solid substances are described to be within the scope of the water-soluble organic solvent in the present invention.

Hereinafter, the preservative and fungicide, pH-adjusting agent, chelating agent, antirusting agent, water-soluble ultraviolet absorber, water-soluble polymer compound, coloring matter-solubilizing agent, antioxidant, and surfactant, which are all used as the ink preparation agent, will be described.

Examples of the fungicide include sodium dehydroacetate, sodium benzoate, sodium pyridinethion-1-oxide, p-hydroxybenzoic acid ethyl ester, 1,2-benzisothiazolin-3-one and salts thereof, and the like. These are preferably used in an amount of 0.02% to 1.00% by mass in the ink composition.

Examples of the preservative include organic sulfur-based, organic nitrogen sulfur-based, organic halogen-based, haloallylsulfone-based, iodopropargyl-based, N-haloalkylthio-based, nitrile-based, pyridine-based, 8-oxyquinoline-based, benzothiazole-based, isothiazoline-based, dithiol-based, pyridine oxide-based, nitropropane-based, organotin-based, phenolic, quaternary ammonium salt-based, triazine-based, thiazine-based, anilide-based, adamantane-based, dithiocarbamate-based, brominated indanone-based, benzylbromacetate-based, inorganic salt-based compounds, and the like.

Specific examples of the organic halogen-based compounds include, for example, pentachlorophenol sodium, and specific examples of the pyridine oxide-based compounds include, for example, sodium 2-pyridinethiol-1-oxide. Specific examples of the isothiazoline-based compounds include, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 5-chloro-2-methyl-4-isothiazolin-3-one calcium chloride, and 2-methyl-4-isothiazolin-3-one calcium chloride. Other specific examples of the preservative and fungicide include anhydrous sodium acetate, sodium sorbate, sodium benzoate, and PROXEL® GXL(S) and PROXEL® XL-2 (S) manufactured by Arch Chemicals, Inc. Meanwhile, in the present invention the superscript "®" means registered trademark.

Regarding the pH-adjusting agent, any substance that does not have an adverse effect on the ink to be prepared and that is capable of controlling the pH of the ink to approximately the range of 5 to 11 can be used. Specific examples thereof include, for example, alkanolamines such as diethanolamine, triethanolamine, and N-methyldiethanolamine; alkali-metal hydroxides such as lithium hydroxide, sodium hydroxide, and potassium hydroxide; ammonium hydroxide (aqueous ammonia); alkali-metal carbonates such as lithium carbonate, sodium carbonate, sodium hydrogen carbonate, and potassium carbonate; alkali-metal salts of organic acids, such as potassium acetate; inorganic bases such as sodium silicate and disodium phosphate, and the like.

Specific examples of the chelating agent include, for example, disodium ethylenediaminetetraacetate, sodium nitrilotriaceate, sodium hydroxyethylethylenediaminetriacetate, sodium diethylenetriaminepentaacetate, sodium uracil diacetate, and the like.

Examples of the antirusting agent include, for example, acidic sulfurous acid salts, sodium thiosulfate, ammonium thioglycolate, diisopropylammonium nitrite, pentaerythritol tetranitrate, dicyclohexylammonium nitrite, and the like.

Examples of the water-soluble ultraviolet absorber include, for example, sulfonated benzophenone-based compounds, benzotriazole-based compounds, salicylic acid-based compounds, cinnamic acid-based compounds, and triazine-based compounds.

Examples of the water-soluble polymer compound include polyvinyl alcohol, cellulose derivatives, polyamine, polyimine, and the like.

Examples of the color-solubilizing agent include, for example, ε-caprolactam, ethylene carbonate, urea, and the like.

As the antioxidant, for example, various organic and metal complex-based discoloration preventing agents may be used. Examples of the organic discoloration-preventing agents include hydroquinones, alkoxyphenols, dialkoxyphenols, phenols, anilines, amines, indanes, chromanes, alkoxyanilines, heterocycles, and the like.

Examples of the surfactant include known surfactants such as anionic, cationic, nonionic surfactants and the like.

Examples of anionic surfactants include alkylsulfonic acid salts, alkylcarboxylic acid salts, α-olefinsulfonic acid salts, polyoxyethylene alkyl ether acetic acid salts, N-acylamino acids and salts thereof, N-acylmethyltaurine salts, alkylsulfate polyoxyalkyl ether sulfuric acid salts, alkylsulfate polyoxyethylene alkyl ether phosphoric acid salts, rosin acid soaps, castor oil sulfate ester salts, lauryl alcohol sulfate ester salts, alkylphenolic phosphate esters, alkylated phosphate esters, alkylaryl sulfonic acid salts, diethyl sulfosuccinic acid salts, diethylhexyl sulfosuccinic acid salts, dioctyl sulfosuccinic acid salts, and the like.

Examples of cationic surfactants include 2-vinylpyridine derivatives, poly-4-vinylpyridine derivatives, and the like.

Examples of amphoteric surfactants include lauryldimethylamino acetate betaine, 2-alkyl-2-N-carboxymethyl-N-hydroxyethylimidazolinium betaine, coconut oil fatty acid amidepropyldimethylamino acetate betaine, polyoctyl polyaminoethylglycine, imidazoline derivatives, and the like.

Examples of nonionic surfactants include ethers such as polyoxyethylene nonyl phenyl ether, polyoxyethylene octyl phenyl ether, polyoxyethylene dodecyl phenyl ether, polyoxyethylene oleyl ether, polyoxyethylene lauryl ether, and polyoxyethylene alkyl ether; esters such as polyoxyethylene oleic acid esters, polyoxyethylene distearic acid esters, sorbitan laurate, sorbitan monostearate, sorbitan monooleate, sorbitan sesquioleate, polyoxyethylene monooleate, and polyoxyethylene stearate; acetylene glycols (alcohols) such as 2,4,7,9-tetramethyl-5-decyne-4,7-diol, 3,6-dimethyl-4-octyne-3,6-diol, and 3,5-dimethyl-1-hexyn-3-ol; trade name: Surfynol 104, 105, 82, and 465, and Olfine STG, manufactured by Nissin Chemical Industry Co., Ltd.; and polyglycol ethers (for example, Tergitol 15-S-7 and the like manufactured by Sigma-Aldrich Co.); and the like.

The ink preparation agents described above are used singly or as mixtures.

The ink composition of the present invention is obtained by mixing the various components described above in an arbitrary order and stirring the mixture. The ink composition thus obtained may be subjected to precise filtration with a membrane filter or the like in order to eliminate contaminants, as desired, and if the ink composition is to be used in inkjet recording, it is preferable to carry out the filtration. The pore size of the filter to carry out precise filtration is usually 1 μm to 0.1 μm, and preferably 0.8 μm to 0.1 μm.

The ink composition of the present invention can be used in various fields, but is suitable for aqueous writing inks, aqueous printing inks, information recording inks, and the like. It is particularly preferable to use the ink composition as an ink for inkjet recording, and the ink composition is suitably used in the inkjet recording method of the present invention that will be described below.

The inkjet recording method of the present invention is a method of using the ink composition of the present invention as an ink, performing recording by discharging droplets of the ink according to the recording signals, and attaching the ink droplets to a record-receiving material. In the inkjet recording method of the present invention, there are no particular limitations on the ink head, ink nozzles, and the like that are used at the time of recording, and those can be appropriately selected according to the purpose.

This recording method can be carried out by using a known method, for example, a charge-control system that discharges ink by utilizing an electrostatic attraction force; a drop-on-demand system (pressure pulse system) that utilizes the vibration pressure of a piezoelectric element; an acoustic inkjet system that converts electrical signals into acoustic beams, irradiates ink with the beams, and discharges the ink by utilizing radiation pressure; and a thermal inkjet (BUBBLEJET (registered trademark)) system that heats ink to form bubbles and utilizes the pressure resulting therefrom.

There are no particular limitations on the record-receiving material that is used in the inkjet recording method of the present invention, but examples thereof include communication sheets such as paper and films; fabrics or cloths (cellulose, nylon, wool, and the like), leather, and base materials for color filter, and among them, communication sheets are preferred.

Regarding these communication sheets, a sheet that has been surface treated, specifically, a base material such as paper, a synthetic paper, or a film provided with an ink-receiving layer, is preferred. The ink-receiving layer is provided by a method such as, for example, impregnating or coating the base material described above with a cationic polymer; or applying a porous white inorganic substance capable of absorbing the coloring matters in the ink, such as porous silica, an alumina sol, or a special ceramic, together with a hydrophilic polymer such as polyvinyl alcohol or polyvinylpyrrolidone, to the surface of the base material.

A communication sheet provided with such an ink-receiving layer is usually called a paper (film) for inkjet exclusive use, a glossy paper (film), or the like. Specific examples thereof include trade names: PROFESSIONAL PHOTO PAPER, SUPER PHOTO PAPER, and MATTE PHOTO PAPER, all manufactured by Canon, Inc.; trade names: PHOTO PAPER (GLOSSY), PM MATTE PAPER, and CRISPIA, all manufactured by Seiko Epson Corp.; and trade names: ADVANCE PHOTO PAPER, PREMIUM PLUS PHOTO PAPER, and PREMIUM GLOSSY FILM or PHOTO PAPER, all manufactured by Hewlett-Packard Japan, Ltd., and these can be purchased as commercially available products. In addition, plain paper also can be used without any problem.

Among the communication sheets described above, it is known that an image recorded on a sheet coated with a porous white inorganic substance on the surface particularly undergoes discoloration and fading to a large extent due to ozone gas. However, since the ink composition of the present invention has excellent ozone-gas resistance, the ink composition exhibits a significant effect even when used for inkjet recording on such a record-receiving material.

In order to perform recording on a record-receiving material by the inkjet recording method of the present invention, for example, a vessel containing the ink composition described above is attached at a predetermined position of an inkjet printer, and recording may be performed on the record-receiving material by the method described above.

The inkjet recording method of the present invention can use the black ink composition of the present invention in combination with ink compositions of various colors such as, for example, known magenta, cyan and yellow such as described above, and optionally, green, blue (or violet), and red (or orange).

The ink compositions of each color are filled in each of the vessels, respectively, and each of the vessels is loaded on prescribed position of an ink jet printer similarly to the vessel containing the black ink composition of the present invention, and used for ink jet recording.

The colored material of the present invention means a material colored with any one of the following three [three of these items a) to c)]:

a) the azo compound, the tautomer thereof, or the salt of the azo compound or the tautomer according to any one of the first to eighth aspects;

b) the aqueous ink composition according to the ninth or tenth aspect; or c) the inkjet recording method according to the eleventh aspect.

There are no particular limitations on the material to be colored, but preferred examples thereof include the record-receiving materials used in the above-described inkjet recording method.

The azo compound of the present invention is a black coloring matter. This compound can be easily synthesized and is inexpensive, and since this compound has the feature of low color saturation, the compound exhibits a more preferred hue as black. Furthermore, since the compound has excellent water-solubility, the compound has satisfactory filterability through a membrane filter in the process for preparing an ink composition.

Furthermore, the ink composition of the present invention containing the azo compound is an aqueous black ink composition, and the ink composition does not exhibit solid precipitation, change of properties, color change, or the like even after long-term storage, and has satisfactory storage stability.

The image recorded with the ink composition of the present invention exhibits excellent ozone-gas resistance, very high print density, low color-rendering properties, and low color saturation, and has a high-quality black hue. The image is also excellent in various fastness properties such as light resistance, moisture resistance, and water resistance. Furthermore, when used in combination with ink compositions respectively containing magenta, cyan and yellow coloring matters, full-color inkjet recording with various fastness properties that are excellent, and excellent storage properties can be achieved.

As such, since an ink composition containing the azo compound of the present invention can be used as an ink for inkjet recording or handwriting, and also exhibits excellent discharge stability, the ink composition is suitable as an ink for inkjet recording in particular.

EXAMPLES

Hereinafter, the present invention will be specifically described by way of Examples, but the present invention is not intended to be limited by the following Examples.

Herein, unless particularly stated otherwise, the units "parts" and "percent (%)" are on a mass basis.

Unless particularly stated otherwise, various operations such as synthesis reactions and crystallization were all carried out under stirring.

In the various formulas described below, acidic functional groups such as sulfo and carboxy are indicated in the form of free acids.

The pH values and reaction temperatures in the synthesis reactions all represent measured values in the reaction systems.

Furthermore, the maximum absorption wavelengths (λmax) of the compounds synthesized were measured in an aqueous solution at pH 7 to 8, and for the compounds thus measured, their measured values are described in the Examples.

In addition, the azo compounds of the present invention synthesized in the following Examples all exhibited a solubility in water of 100 g/liter or higher.

(A) Synthesis of dyes

Example 1

Step 1

51.8 parts of 4-chloro-3-nitroaniline was dissolved in 60.0 parts of N-methyl-2-pyrrolidone, and 35.2 parts of acetic anhydride was added dropwise thereto over about 15 minutes. After the dropwise addition, the mixture was allowed to react for 2 hours at 40° C. to 50° C., and then the reaction liquid was added to 400 parts of water. The mixture was stirred for 30 minutes at room temperature, subsequently the solid thus precipitated out was filtered, and the solid thus obtained was washed with 100 parts of water on a funnel, separated, and dried. Thus, 63.0 parts of the compound represented by the following formula (14) was obtained.

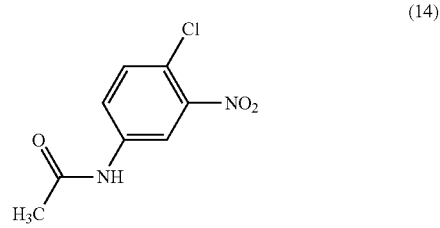

Step 2

42.9 parts of the compound represented by the formula (14) and obtained in Example 1 (Step 1) described above was dissolved in 115.0 parts of N-methyl-2-pyrrolidone, and 40.9 parts of sodium 3-mercaptopropanesulfonate and 29.0 parts of potassium carbonate were added thereto. After the addition, the mixture was heated to 130° C. to 140° C., and was allowed to react for 2 hours at the same temperature. 3.6 parts of sodium 3-mercaptopropanesulfonate was further added thereto, and then the mixture was allowed to react for 1 hour at 130° C. to 140° C. The reaction mixture was cooled to 60° C., and then the reaction liquid was added to 700 parts of 2-propanol. The mixture was cooled to room temperature, and then the solid thus obtained was separated by filtration. The wet cake thus obtained was dissolved in 300 parts of water, subsequently the solution was adjusted to pH 3.0 to 4.0 by the addition of 35% hydrochloric acid, and then the solution was salted out with sodium chloride. The solid thus precipitated out was separated by filtration, and thereby 205.3 parts of a compound represented by the following formula (15) was obtained as wet cake.

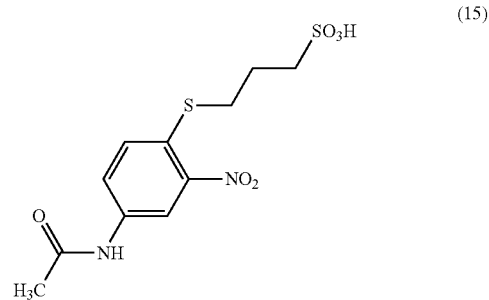 [SMILES: CC(=O)Nc1ccc(SCCCS(=O)(=O)O)c([N+](=O)[O-])c1]

Step 3

102.6 parts of the wet cake of the compound represented by the formula (15) and obtained in Example 1 (Step 2) described above, 1.6 parts of activated charcoal, and 0.4 parts of anhydrous iron(III) chloride were added to 150 parts of water, the mixture was heated to 60° C., and then 15.9 parts of 80% hydrazine hydrate was added dropwise thereto over about 30 minutes. The mixture was heated to 90° C., and then the mixture was allowed to react for 1.5 hours at the same temperature. The mixture was cooled to 40° C., subsequently insoluble matters were removed by filtration, and the filtrate was cooled to room temperature. The filtrate was adjusted to pH 1.0 to 1.5 by adding 50% sulfuric acid, the solid thus precipitated out was separated by filtration, and thus 62.3 parts of the compound represented by the following formula (16) was obtained as wet cake.

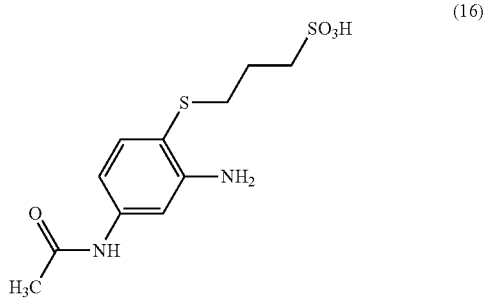 [SMILES: CC(=O)Nc1ccc(SCCCS(=O)(=O)O)c(N)c1]

Step 4

12.6 parts of 5-amino-2-chlorobenzenesulfonic acid represented by the following formula (17) was added to 40 parts of water, and then a 25% aqueous solution of sodium hydroxide was added thereto to obtain an aqueous solution at pH 4.0 to 5.0. 25 parts of 35% hydrochloric acid was added thereto, subsequently 12.6 parts of a 40% aqueous solution of sodium nitrite was added thereto, and the mixture was allowed to react for about 30 minutes. To this, 1.5 parts of sulfamic acid was added, subsequently the mixture was stirred for 5 minutes, and thus a diazo reaction liquid was obtained. On the other hand, 32.4 parts of the wet cake of the compound represented by the formula (16) and obtained in Example 1 (Step 3) described above was added to 200 parts of water, and then a 25% aqueous solution of sodium hydroxide was added thereto to obtain an aqueous solution at pH 4.0 to 5.0. This aqueous solution was added dropwise to the diazo reaction liquid obtained as described above, over about 5 minutes. After the dropwise addition, while the pH was maintained at 2.0 to 2.5 by adding a 15% aqueous solution of sodium carbonate, the mixture was allowed to react for 3 hours, and then the mixture was subjected to salting-out by adding sodium chloride. The solid thus precipitated out was separated by filtration, and thus 31.5 parts of a compound represented by the following formula (18) was obtained as wet cake.

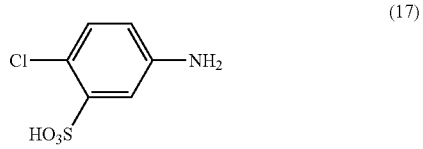

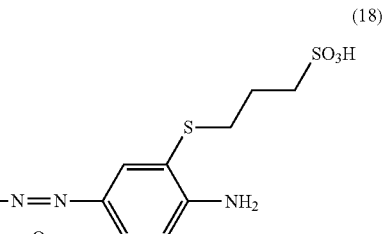

Step 5

The entire amount of the wet cake of the compound represented by the formula (18) and obtained in Example 1 (Step 4) described above was added to 40 parts of water, and then a 25% aqueous solution of sodium hydroxide was added thereto to obtain an aqueous solution at pH 6.0 to 7.0. 24.8 parts of 35% hydrochloric acid was added thereto, subsequently 9.8 parts of a 40% aqueous solution of sodium nitrite was added thereto, and the mixture was allowed to react for about 30 minutes. 2.0 parts of sulfamic acid was added thereto, the mixture was stirred for 5 minutes, and thus a diazo reaction liquid was obtained.

On the other hand, 30.8 parts of the wet cake of the compound represented by the formula (16) and obtained in Example 1 (Step 3) described above was added to 250 parts of water, and then a 25% aqueous solution of sodium hydroxide was added thereto to obtain an aqueous solution at pH 4.0 to 5.0. This aqueous solution was added dropwise over about 5 minutes to the diazo reaction liquid obtained as described above. After the dropwise addition, while the pH was maintained at 2.0 to 2.5 by adding a 15% aqueous solution of sodium carbonate, the mixture was allowed to react for 3 hours, and then the mixture was subjected to salting-out by adding sodium chloride. The solid thus precipitated out was separated by filtration, and thus 90 parts of the compound represented by the following formula (19) was obtained as wet cake.

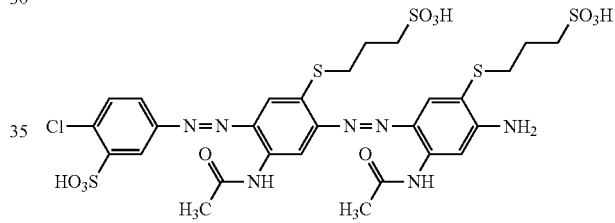

Step 6

45 parts of the wet cake of the compound represented by the formula (18) and obtained in Example 1 (Step 4) described above was added to 250 parts of water, and the compound was dissolved by stirring. 16.5 parts of 35% hydrochloric acid was added thereto, subsequently 4.7 parts of a 40% aqueous solution of sodium nitrite was added thereto, and the mixture was stirred for about 30 minutes. To this, 2.0 parts of sulfamic acid was added, the mixture was stirred for 5 minutes, and thus a diazo reaction liquid was obtained.

On the other hand, 5.5 parts of the compound represented by the following formula (20) and obtainable by the method described in Japanese Unexamined Patent Application, Publication No. 2004-083492, was added to 60 parts of water, and a 25% aqueous solution of sodium hydroxide was added thereto to obtain an aqueous solution at pH 4.5 to 5.5. This aqueous solution was added dropwise over about 5 minutes to the diazo reaction liquid obtained as described above. After the dropwise addition, while the pH was maintained at 2.0 to 3.0 by adding a 15% aqueous solution of sodium carbonate, the mixture was allowed to react for 3 hours. The pH was adjusted to 4.5 by adding a 15% aqueous solution of sodium carbonate, and then 350 parts of methanol was added thereto. The solid thus precipitated out was separated by filtration, and thus 96.6 parts of the compound represented by the following formula (21) was obtained as wet cake.

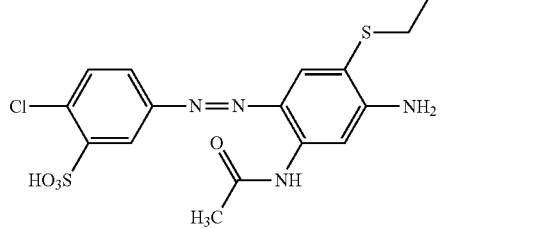

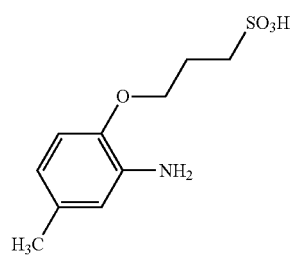

(20)

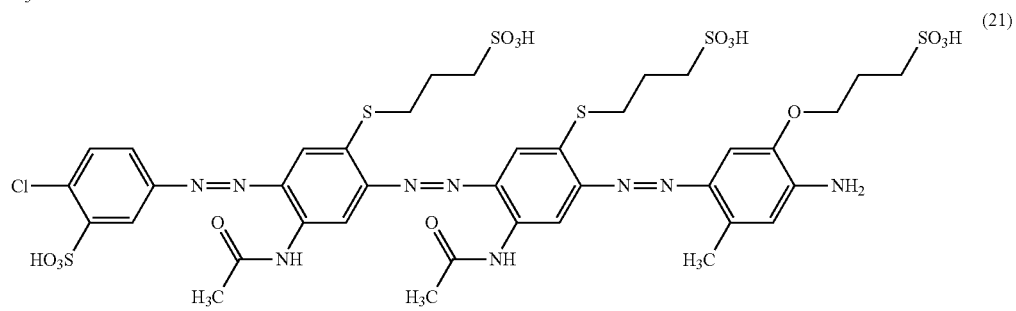

(21)

Step 7

32.2 parts of the wet cake of the compound represented by formula (21) and obtained in Example 1 (Step 6) described above was added to 170 parts of water, and the compound was dissolved by stirring. 5.2 parts of 35% hydrochloric acid was added thereto, subsequently 1.5 parts of a 40% aqueous solution of sodium nitrite was added thereto, and the mixture was stirred for about 30 minutes. To this, 1.0 part of sulfamic acid was added, the mixture was stirred for 5 minutes, and thus a diazo reaction liquid was obtained.

On the other hand, 2.2 parts of a compound represented by the following formula (22) and obtained by the method described in Patent Document 4 was added to 60 parts of water, and a 25% aqueous solution of sodium hydroxide was added thereto to adjust the mixture to pH 7.5 to 8.5. Thus, an aqueous solution was obtained. To this aqueous solution, the diazo reaction liquid obtained as described above was added dropwise over about 30 minutes at 15° C. to 30° C. At this time, the pH of the reaction liquid was maintained at 7.5 to 8.5 by adding an aqueous solution of sodium carbonate, and while the same temperature and pH adjustment were maintained, the reaction liquid was allowed to react for another 2 hours. Sodium chloride was added to the reaction liquid to salt out, the solid thus precipitated out was separated by filtration, and thus 29.5 parts of wet cake was obtained. The wet cake thus obtained was dissolved in 100 parts of water, and the pH was adjusted to 7.0 to 7.5 with 35% hydrochloric acid. Subsequently, 80 parts of methanol was added thereto, and the solid thus precipitated out was separated by filtration. The wet cake thus obtained was dissolved again in 60 parts of water, and then 90 parts of methanol was added thereto. A precipitated solid was separated by filtration and dried, and thereby 6.3 parts of the compound represented by the following formula (23) of the present invention was obtained as a sodium salt. λmax: 589 nm.

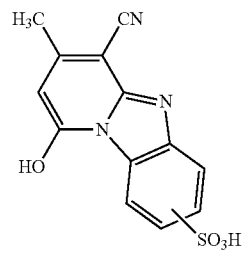

(22)

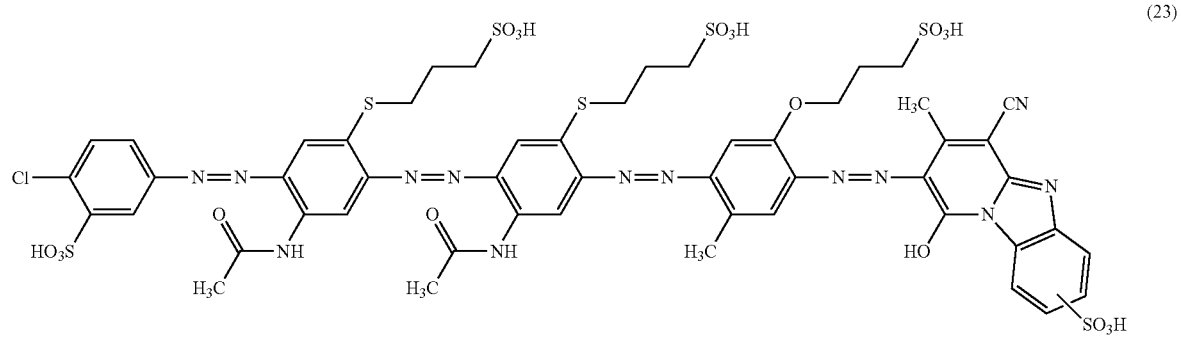

(23)

Example 2

Sodium salt of 6.3 parts of the compound represented by the formula (23) and obtained in Example 1, and 14 parts of lithium chloride were added to 140 parts of water, and the mixture was stirred to obtain an aqueous solution. 400 parts of 2-propanol was added thereto, the solid thus precipitated out was separated by filtration, and thus wet cake was obtained. The wet cake thus obtained and 12.5 parts of lithium chloride were added to 150 parts of water again, and the mixture was stirred to obtain an aqueous solution. 350 parts of 2-propanol was added thereto, the solid thus precipitated out was separated by filtration, and thus wet cake was obtained. The wet cake thus obtained was dissolved in 80 parts of water, and 150 parts of 2-propanol was added thereto. The solid thus precipitated out was separated by filtration, and thus wet cake was obtained. The wet cake thus obtained was dissolved again in 40 parts of water, and 100 parts of 2-propanol was added thereto. The solid thus precipitated out was separated by filtration and dried. Thereby, 4.5 parts of the compound represented by the formula (23) of the present invention was obtained as a mixed salt with sodium and lithium. λmax: 586 nm.

Example 3

Step 1

15.2 parts of 2-methyl-6-nitroaniline was dissolved in 300 parts of methanol. The solution thus obtained was transferred into an autoclave, 2.0 parts of 5% Pd/carbon was added thereto, and the mixture was allowed to react at 20° C. to 30° C. at a hydrogen pressure of 0.2 MPa to 0.5 MPa, until the absorption of hydrogen had run its course. Thereafter, the reaction was continued for another 30 minutes at the same temperature. The catalyst (5% Pd/carbon) was separated by filtration, and thereby, a solution (filtrate) containing the compound represented by the following formula (24) was obtained.

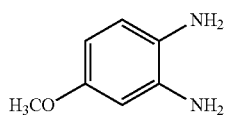

(24)

Step 2

13.0 parts of methyl cyanoacetate was added to 200 parts of the solution containing the compound represented by the formula (24) and obtained in Example 3 (Step 1), and the mixture was heated to reflux for 30 minutes. Thereafter, methanol was concentrated under reduced pressure, and 100 parts of water was added thereto, followed by sodium carbonate to adjust the pH 7.0 to 7.5. The solid thus precipitated out was separated by filtration and dried. Thereby, 8.3 parts of the compound represented by the following formula (25) was obtained.

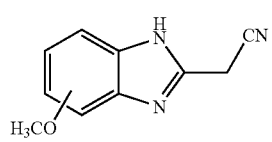

(25)

Step 3

8.3 parts of the compound represented by the formula (25), 12.0 parts of 28% sodium methoxide, and 7.2 parts of methyl acetoacetate were added to 100 parts of ethanol, and the mixture was heated to reflux for 30 minutes. Subsequently, ethanol was concentrated under reduced pressure, and 100 parts of water was added thereto, followed by 35% hydrochloric acid to adjust the pH to 7.0 to 7.5. The solid thus precipitated out was separated by filtration and dried. Thereby, 11.1 parts of the compound represented by the following formula (26) was obtained. The compound represented by the following formula (26) and thus obtained was a mixture of compounds having a methoxy group substituted at position b or c.

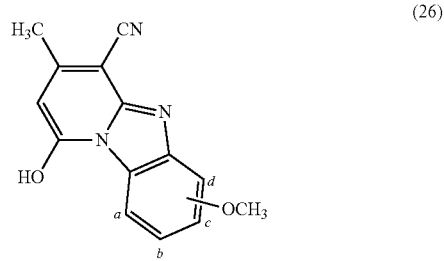

(26)

Step 4

5.6 parts of the compound represented by the formula (26) was slowly added to 77 parts of 8% fuming sulfuric acid at 5° C. to 10° C., and then the mixture was allowed to react for 1.5 hours at the same temperature. The reaction liquid was added dropwise to 150 parts of ice water over about 10 minutes, and the mixture was stirred for 30 minutes at 65° C. to 70° C. The solid thus precipitated out was separated by filtration, and thereby 24.4 parts of wet cake of the compound represented by the following formula (27) was obtained. The compound represented by the following formula (27) was a mixture of a compound in which the methoxy group was substituted at position b and the substitution position of the sulfo group was a, c, or d, or a compound in which the methoxy group was substituted at position c and the substitution position of the sulfo group was a, b, or d.

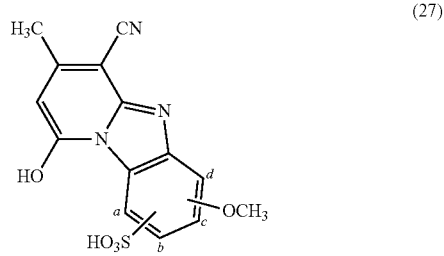

(27)

Step 5

The operation was carried out in the same manner as in Example 1 (Step 7), except that 7.2 parts of the wet cake of the compound represented by the formula (27) and obtained in Example 3 (Step 4) was used for Example 1 (Step 7), instead of using 2.2 parts of the compound represented by the formula (22), and thus 6.3 parts of the compound represented by the following formula (28) of the present invention was obtained as a sodium salt. The coloring matter thus obtained was a mixed coloring matter including 2 to 6 kinds of compounds in which the methoxy group in the following formula (28) was substituted at position b and the substitution position of the sulfo group was a, c, or d, or a compound in which the methoxy group was substituted at position c and the substitution position of the sulfo group was a, b, or d.

pressure, and 150 parts of water was added thereto, followed by sodium carbonate to adjust the pH to 7.0 to 7.5. The solid thus precipitated out was separated by filtration and dried, and thereby 8.4 parts of the compound represented by the following formula (31) was obtained.

Meanwhile, the compound represented by the following formula (30) was obtained by the method described in Patent Document 9.

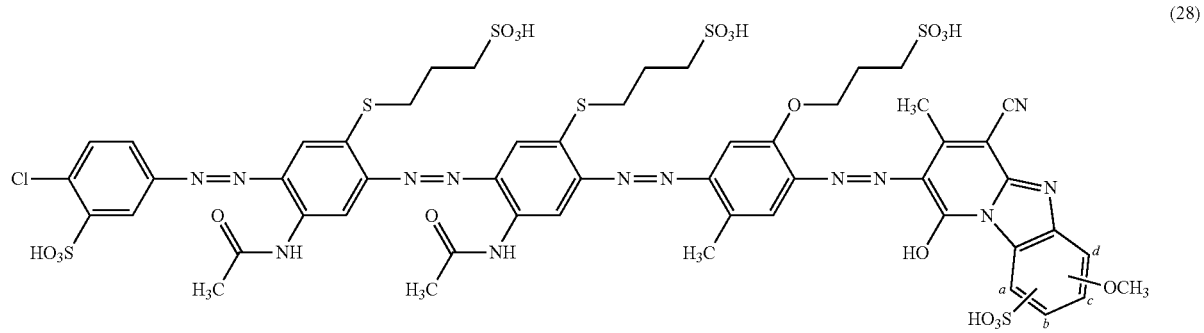

(28)

Example 4

The operation was carried out in the same manner as in Example 2, except that 8.8 parts of sodium salt of the compound represented by the formula (28) and obtained in Example 3 (Step 5) was used instead of 6.3 parts of sodium salt of the compound represented by the formula (23), and 4.5 parts of the compound represented by the formula (28) of the present invention was obtained as a mixed salt with sodium and lithium. λmax: 592 nm.

Example 5

Step 1

15.2 parts of 2-methyl-6-nitroaniline was dissolved in 300 parts of methanol. The solution thus obtained was transferred into an autoclave, 2.0 parts of 5% Pd/carbon was added thereto, and the mixture was allowed to react at 20° C. to 30° C. and at hydrogen pressure of 0.2 MPa to 0.5 MPa under stirring, until the absorption of hydrogen had run its course. Thereafter, the reaction was continued for another 30 minutes at the same temperature. The catalyst (5% Pd/carbon) was separated by filtration, and thereby a solution (filtrate) containing the compound represented by the following formula (29) was obtained.

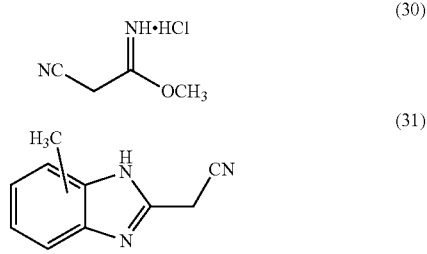

(30)

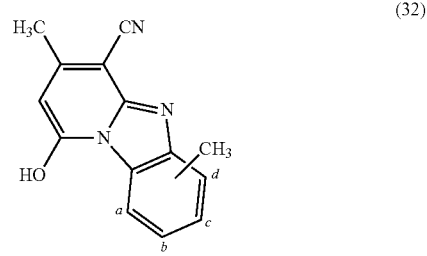

(31)

Step 3

8.4 parts of a compound represented by the following formula (31), 12.3 parts of 28% sodium methoxide, and then 7.4 parts of methyl acetoacetate were added to 100 parts of ethanol, and the mixture was heated to reflux for 30 minutes. Subsequently, ethanol was concentrated under reduced pressure, and 150 parts of water was added thereto, followed by 35% hydrochloric acid to adjust the pH to 7.0 to 7.5. The solid thus precipitated out was separated by filtration and dried, and thereby, 10.0 parts of the compound represented by the following formula (32) was obtained. The compound represented by the following formula (32) was a compound in which the methyl group was substituted at position a or d.

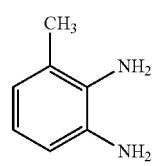

(29)

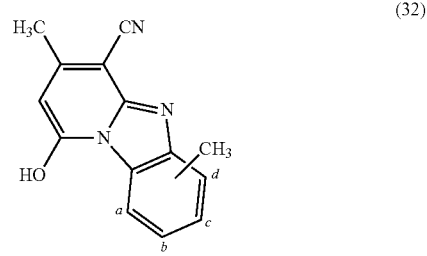

(32)

Step 2

13.0 parts of a compound represented by the following formula (30) was added to 200 parts of the solution containing the compound represented by the formula (29), and the mixture was heated to reflux for 30 minutes under stirring. Subsequently, the reaction liquid was concentrated under reduced

Step 4

5.0 parts of the compound represented by the formula (32) was slowly added to 102 parts of 3% fuming sulfuric acid at 5° C. to 10° C., and then the mixture was stirred for 1 hour at the same temperature. The reaction liquid was added dropwise to 240 parts of ice water over about 10 minutes, the solid thus precipitated out was separated by filtration, and thereby, 14.7 parts of wet cake containing the compound represented by the following formula (33) was obtained. The compound represented by the following formula (33) was a compound in which the methyl group was substituted at position a and the substitution position of the sulfo group was c, or a compound in which the methyl group was substituted at position d and the substitution position of the sulfo group was b.

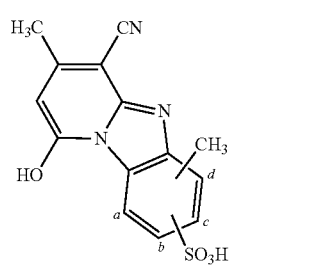

(33)

Step 5

The operation was carried out in the same manner as in Example 1 (Step 7), except that 6.0 parts of the wet cake of the compound represented by the formula (33) and obtained in Example 5 (Step 4) was used instead of 2.2 parts of the compound represented by the formula (22), and thus 6.0 parts of the compound represented by the following formula (34) of the present invention was obtained as sodium salt. The coloring matter thus obtained was a mixed coloring matter including 2 to 6 kinds of compounds in which the methoxy group in the following formula (34) was substituted at position b and the substitution position of the sulfo group was a, c, or d, or the methoxy group was substituted at position c and the substitution position of the sulfo group was a, b, or c.

Example 6

The operation was carried out in the same manner as in Example 2, except that 8.8 parts of sodium salt of the compound represented by the formula (34) and obtained in Example 5 (Step 5) was used instead of using 6.3 parts of sodium salt of the compound represented by the formula (23), and thus 4.0 parts of a compound represented by the formula (34) of the present invention was obtained as a mixed salt with sodium and lithium. λmax: 590 nm.

Example 7

Step 1

45 parts of the wet cake of the compound represented by the formula (18) and obtained in Example 1 (Step 4) was added to 250 parts of water, and the compound was dissolved by stirring. 16.5 parts of 35% hydrochloric acid was added thereto, subsequently 4.7 parts of a 40% aqueous solution of sodium nitrite was added thereto, and the mixture was stirred for about 30 minutes. 2.0 parts of sulfamic acid was added thereto, the mixture was stirred for 5 minutes, and a diazo reaction liquid was obtained.

On the other hand, 5.8 parts of the compound represented by the following formula (35) and obtainable by a method described in Japanese Unexamined Patent Application, Publication No. 2004-083492 was added to 60 parts of water, a 25% aqueous solution of sodium hydroxide was added thereto to obtain an aqueous solution at pH 4.5 to 5.5. This aqueous solution was added dropwise, over about 5 minutes, to the diazo-reaction liquid obtained as described above. After the dropwise addition, while the pH was maintained at 2.0 to 3.0 by adding a 15% aqueous solution of sodium carbonate, the mixture was allowed to react for 3 hours. The pH was adjusted to 4.5 by adding a 15% aqueous solution of sodium carbonate, and then 350 parts of methanol was added thereto. The solid thus precipitated out was separated by filtration, and thus 94.0 parts of the compound represented by the following formula (36) was obtained as wet cake.

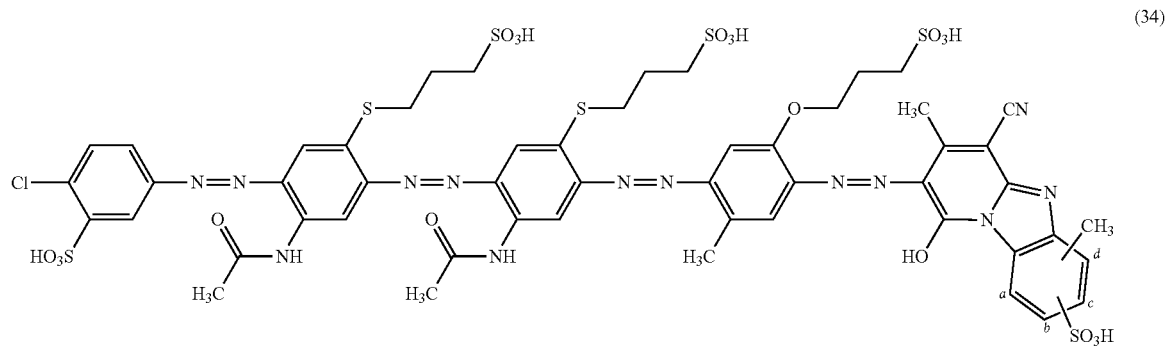

(34)

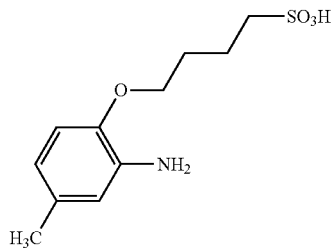

(35)

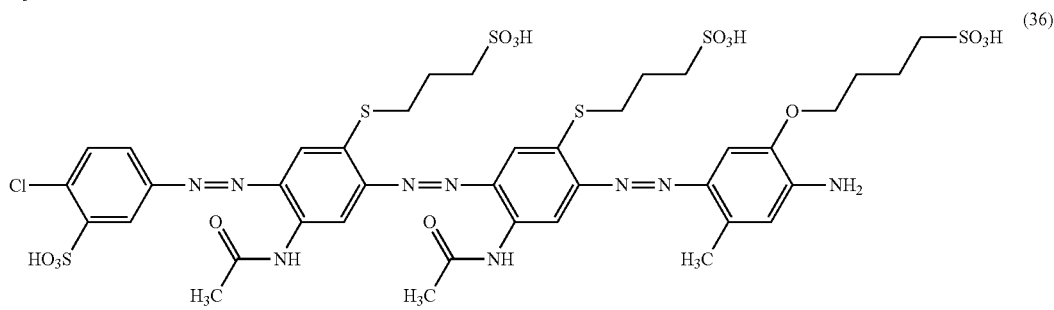

(36)

Step 2

31.3 parts of the wet cake of the compound represented by the formula (36) and obtained in Example 7 (Step 1) as described above was added to 170 parts of water, and the compound was dissolved by stirring. 5.2 parts of 35% hydrochloric acid was added thereto, subsequently 1.5 parts of a 40% aqueous solution of sodium nitrite was added thereto, and the mixture was stirred for about 30 minutes. 1.0 parts of sulfamic acid was added thereto, the mixture was stirred for 5 minutes, and thus a diazo reaction liquid was obtained.

thus 30.0 parts of wet cake was obtained. The wet cake thus obtained was dissolved in 100 parts of water, and the pH was adjusted to 7.0 to 7.5 with 35% hydrochloric acid. Subsequently, 80 parts of methanol was added thereto, and the solid thus precipitated out was separated by filtration. The wet cake thus obtained was dissolved again in 60 parts of water, and then 90 parts of methanol was added thereto. The solid thus precipitated out was separated by filtration and dried, and thereby 6.0 parts of the compound represented by the following formula (37) of the present invention was obtained as sodium salt.

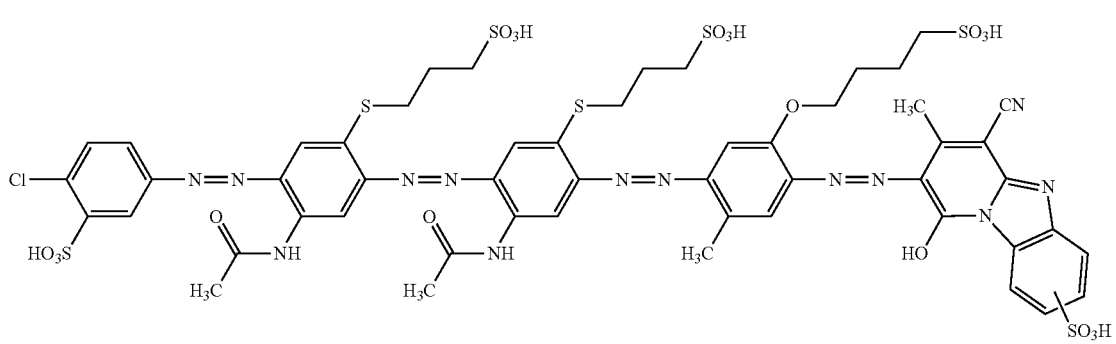

(37)

On the other hand, 2.2 parts of the compound represented by the formula (22) and obtained by the method described in Patent Document 4 was added to 60 parts of water, a 25% aqueous solution of sodium hydroxide was added thereto to adjust the mixture to pH 7.5 to 8.5, and thus an aqueous solution was obtained. To this aqueous solution, the diazo reaction liquid obtained as described above was added dropwise over about 30 minutes at 15° C. to 30° C. At this time, an aqueous solution of sodium carbonate was added thereto to maintain the pH of the reaction liquid at 7.5 to 8.5, and while the same temperature and pH adjustment were maintained, the reaction liquid was allowed to react for another 2 hours. Sodium chloride was added to the reaction liquid to salt out, the solid thus precipitated out was separated by filtration, and

Example 8

The sodium salt of 6.0 parts of the compound represented by the formula (37) and obtained in Example 7, and 14 parts of lithium chloride were added to 140 parts of water, and the mixture was stirred to obtain an aqueous solution. 400 parts of 2-propanol was added thereto, the solid thus precipitated out was separated by filtration, and thus wet cake was obtained. The wet cake thus obtained and 12.5 parts of lithium chloride were added again to 150 parts of water, and the mixture was stirred to obtain an aqueous solution. 350 parts of 2-propanol was added thereto, the solid thus precipitated out was separated by filtration, and thus wet cake was obtained. The wet cake thus obtained was dissolved in 80 parts of water, and 150 parts of 2-propanol was added thereto. The solid thus precipitated out was separated by filtration, and wet cake was obtained. The wet cake thus obtained was dissolved again in 40 parts of water, 100 parts of 2-propanol was added thereto, and the solid thus precipitated out was separated by filtration and dried. Thereby, 4.3 parts of the compound represented by the formula (37) of the present invention was obtained as a mixed salt with sodium and lithium. λmax: 590 nm.

Example 9

The operation was carried out in the same manner as in Example 1 (Step 7), except that 7.2 parts of the wet cake of the compound represented by the formula (27) and obtained in Example 3 (Step 4) was used instead of using 2.2 parts of the compound represented by the formula (22), and thus 5.6 parts of the compound represented by the following formula (38) of the present invention was obtained as sodium salt. The coloring matter thus obtained was a mixed coloring matter including 2 to 6 kinds of compounds in which the methoxy group in the following formula (38) was substituted at position b and the substitution position of the sulfo group was a, c, or d, or the methoxy group was substituted at position c and the substitution position of the sulfo group was a, b, or d.

pore size of 0.45 μm, and the inks thus obtained were designated as Examples 11 to 15. The ink compositions thus obtained will be hereinafter referred to as "inks".

Furthermore, as for water, ion-exchanged water was used. At the time of ink formulation, the pH of the inks was adjusted to pH 7 to 9 with lithium hydroxide, and thereafter, the total amount was adjusted to 100 parts by adding ion-exchanged water. Meanwhile, regarding the surfactant indicated in the following Table 18, trade name: Surfynol 104PG50 manufactured by Nissin Chemical Industry Co., Ltd. was used.

TABLE 18

| Composition of ink composition | |
| --- | --- |
| Component | Number of parts |
| Coloring matter obtained from Example | 3.5 |
| Glycerin | 5.0 |
| Urea | 5.0 |
| N-methyl-2-pyrrolidone | 4.0 |
| Isopropyl alcohol | 3.0 |
| Butyl carbitol | 2.0 |
| Taurine | 0.3 |
| Ethylenediamine tetraacetic acid disodium | 0.1 |

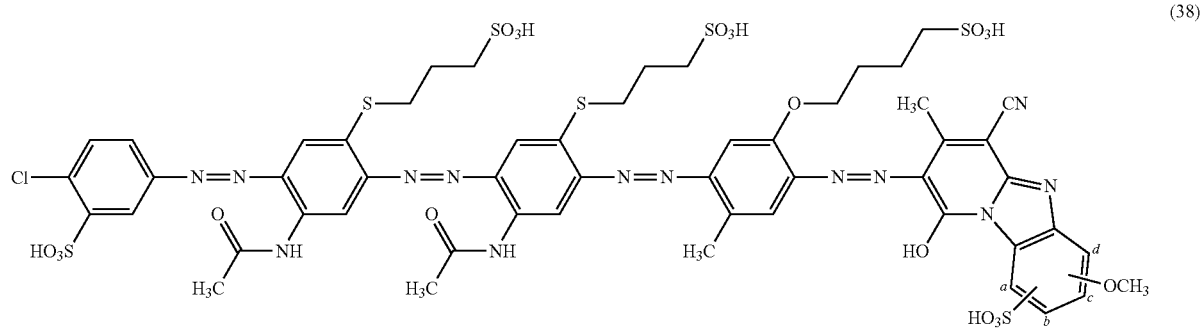

(38)

Example 10

The operation was carried out in the same manner as in Example 7, except that 5.6 parts of sodium salt of the compound represented by the formula (38) and obtained in Example 9 was used instead of using 6.0 parts of sodium salt of the compound represented by the formula (37), and thus 4.0 parts of the compound represented by the formula (38) of the present invention was obtained as a mixed salt with sodium and lithium. λmax: 597 nm.

The coloring matters obtained in Examples 1 to 10 were respectively dissolved in ion-exchanged water, and liquids in which 5% of each of the coloring matters was dissolved in water were prepared. The solutions thus obtained were placed in sealed containers and were left to stand for 1 week in a constant-temperature, constant-humidity chamber at 60° C.; however, decomposition of the coloring matters did not occur.

(B) Preparation of Inks

The respective dyes obtained in Examples 2, 4, 6, 8, and 10 were mixed with the various components described in the following Table 18, and thereby black ink compositions of the present invention were obtained. Thereafter, contaminants were separated by filtration with a membrane filter having a TABLE 18-continued

| Composition of ink composition | |
| --- | --- |
| Component | Number of parts |
| Surfactant | 0.1 |
| water | 77.0 |
| total | 100.0 |

Comparative Example 1

An ink for comparison was prepared by the method described in section "(B) Preparation of inks," by using a coloring matter of the following formula (39) as the black coloring matter to be compared. The following various tests carried out on this ink are designated as Comparative Example 1. Meanwhile, the compound of the following formula (39) is the compound (22) described in Example 1 of Japanese Unexamined Patent Application, Publication No. 2008-169374, and the compound was obtained by reattempting the method described in the document.

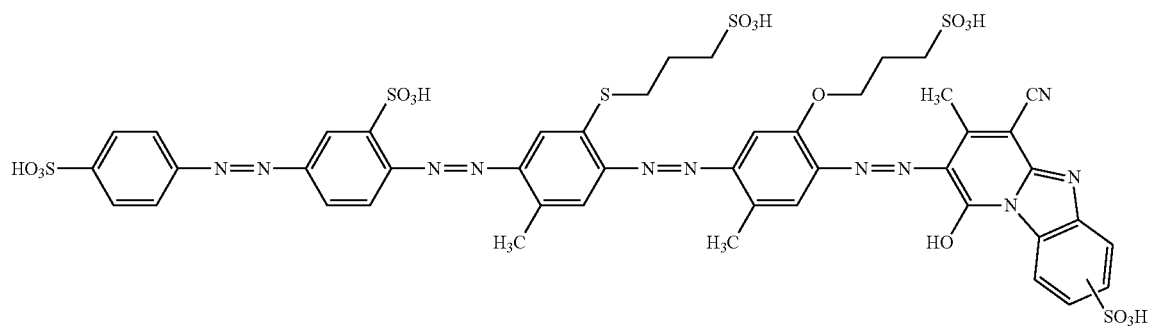

(39)

Comparative Example 2

An ink for comparison was prepared by the method described in section "(B) Preparation of inks," by using a coloring matter of the following formula (40) as the black coloring matter to be compared. The following various tests carried out on this ink are designated as Comparative Example 2. Meanwhile, the compound of the following formula (40) is the compound (25) described in Example 4 of Japanese Unexamined Patent Application, Publication No. 2008-169374, and the compound was obtained by reattempting the method described in the document.

coloring matter of the following formula (41) as the black coloring matter to be compared. The following various tests carried out on this ink are designated as Comparative Example 3. Meanwhile, the compound of the following formula (41) is the compound (28) described in Example 5 of Japanese Unexamined Patent Application, Publication No. 2008-169374, and the compound was obtained by reattempting the method described in the document.

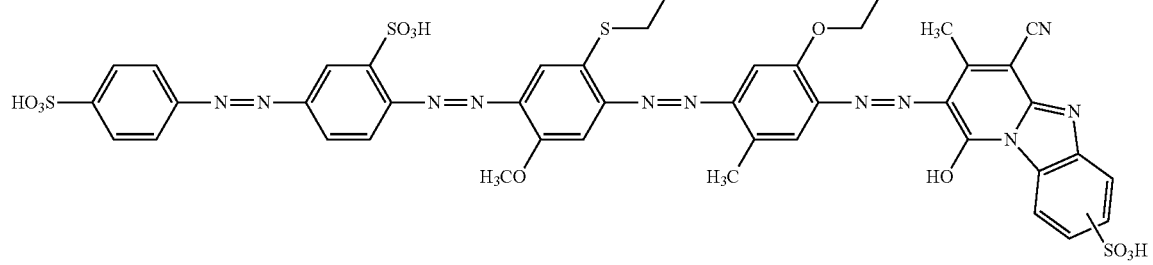

(40)

Comparative Example 3

An ink for comparison was prepared by the method described in section "(B) Preparation of inks," by using a

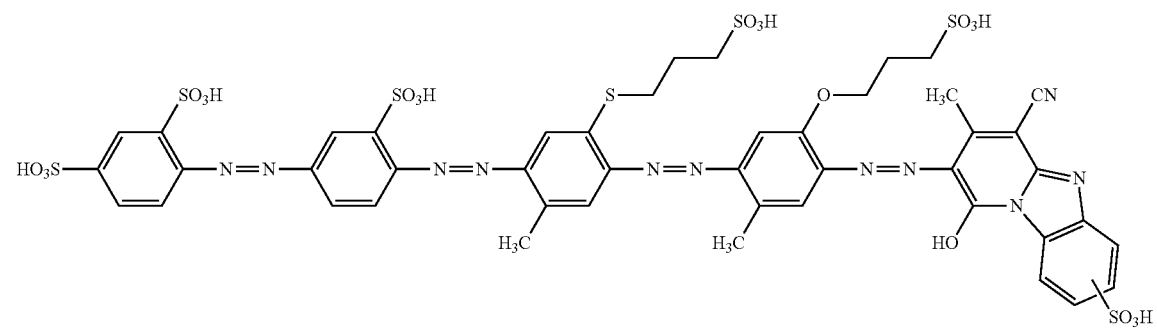

(41)

(C) Inkjet Recording

Inkjet recording was performed on glossy papers 1 to 3 described below, by using the ink obtained as described above, and using an inkjet printer manufactured by Canon, Inc., trade name: PIXUS iP4500.

Glossy paper 1: Glossy paper manufactured by Canon, Inc., trade name: PHOTO PAPER GLOSSY PRO [PT-101A420]

Glossy paper 2: Glossy paper manufactured by Brother Industries, Ltd., trade name: PHOTO GLOSSY PAPER [BP71GA4]

Glossy paper 3: Glossy paper manufactured by Fujifilm Corp., trade name: PHOTO FINISH PRO [WPA430PRO]

At the time of printing, image patterns were produced so as to obtain gradation of six levels at densities of 100%, 80%, 60%, 40%, 20%, and 10%, and recorded materials with gradation from dark black to light black were obtained. The following evaluation tests were carried out by using these as specimens.

(D) Evaluation of Recorded Images

The respective recorded images obtained by using the inks of Examples 11 to 15 and Comparative Examples 1 to 3 were subjected to an evaluation by measuring the density change in the images before and after a test.

The density change in a recorded image was measured by measuring the color of a gradation part in which the reflected density, Dk value, of the recorded image before the test was closest to 1.0, by using a colorimeter manufactured by Gretag-Macbeth GmbH, trade name: SPECTROEYE. All the colorimetric measurements were made by using DIN as a density standard, under the conditions of a 2° viewing angle and a D65 light source. In the present test, all of the specimens had areas where the reflected density, Dk value, in a gradation area with a density of 60% was close to 1.0. Specific test methods are as follows.

(E) Ozone-Gas Resistance Test

The respective recorded images obtained by using the inks of Examples 11 to 15 and Comparative Examples 1 to 3 were dried naturally for 24 hours after printing, and the respective specimens were left to stand for 8 hours under the conditions of an ozone concentration of 40 ppm, a humidity of 60% RH, and a temperature of 24° C. by using trade name: OZONE WEATHER-O-METER manufactured by Suga Test Instruments Co., Ltd.

After completion of the test, the color was measured by using the aforementioned colorimeter, and the residual ratio of coloring matter was determined from the formula: (reflected density Dk after test/reflected density Dk before test)× 100(%). Thus, an evaluation was carried out on the basis of the following criteria. In the evaluation thus obtained, a specimen having a higher residual ratio exhibited less fading caused by ozone gas, which was considered superior. The results are presented in the following Table 19.

A: Residual ratio: 98% or higher

B: Residual ratio: equal to or higher than 95% and less than 98%

C: Residual ratio: equal to or higher than 90% and less than 95%

D: Residual ratio: less than 90%

TABLE 19

|  | Glossy paper 1 | Glossy paper 2 | Glossy paper 3 |
|---|---|---|---|
| Example 11 | A | A | A |
| Example 12 | A | A | A |
| Example 13 | A | A | A |
| Example 14 | A | A | A |
| Example 15 | B | A | A |
| Comparative Example 1 | D | C | C |
| Comparative Example 2 | C | C | C |
| Comparative Example 3 | D | D | D |

As is obvious from the results of Table 19, it was clearly shown that the respective inks of the Examples had superb ozone-gas resistance as compared with the inks of Comparative Examples 1 to 3. That is, it was obvious that the inks had high residual ratios of the Dk density after the ozone-gas resistance test, and the inks had improved fading properties against ozone gas.

Furthermore, it was obvious that the inks provided high-quality recorded images without having the fastness properties markedly degraded depending on the medium.

INDUSTRIAL APPLICABILITY

The azo compound of the present invention and an ink composition containing it are suitably used in black inks for various recording applications such as handwriting instruments, and particularly for inkjet recording.

The invention claimed is:

1. An azo compound represented by the following formula (1), a tautomer thereof, or a salt of the azo compound or the tautomer:

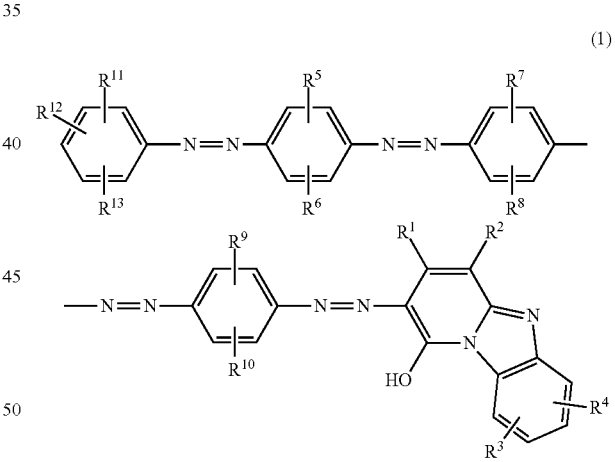

wherein, $R^1$ represents a (C1-C4) alkyl group; a (C1-C4) alkyl group substituted with a carboxy group; a phenyl group; a phenyl group substituted with a sulfo group; or a carboxy group, $R^2$ represents a cyano group; a carbamoyl group; or a carboxy group, $R^3$ and $R^4$ each independently represents a hydrogen atom; a (C1-C4) alkyl group; a halogen atom; a (C1-C4) alkoxy group; or a sulfo group, $R^5$ represents a (C1-C4) alkylthio group; or a (C1-C4) alkylthio group substituted with at least one kind of group selected from the group consisting of a hydroxy group, a sulfo group, and a carboxy group, $R^6$ represents a (C1-C4) alkylcarbonylamino group, $R^7$ represents a (C1-C4) alkylthio group; or a (C1-C4) alkylthio group substituted with at least one kind of group selected from the group consisting of a hydroxy group, a sulfo group, and a carboxy group, $R^8$ represents a (C1-C4) alkylcarbonylamino group, $R^9$ and $R^{10}$ each independently represents a hydrogen atom; a carboxy group; a sulfo group; an acetylamino group; a chlorine atom; a (C1-C4) alkyl group; a (C1-C4) alkoxy group; or a (C1-C4) alkoxy group substituted with at least one kind of group selected from the group consisting of a hydroxy group, a (C1-C4) alkoxy group, a sulfo group, and a carboxy group, and $R^{11}$ to $R^{13}$ each independently represents a hydrogen atom; a carboxy group; a sulfo group; a hydroxy group; an acetylamino group; a chlorine atom; a cyano group; a nitro group; a sulfamoyl group; a (C1-C4) alkyl group; a (C1-C4) alkoxy group; a (C1-C4) alkoxy group substituted with at least one kind of group selected from the group consisting of a hydroxy group, a (C1-C4) alkoxy group, a sulfo group and a carboxy group; a (C1-C4) alkylsulfonyl group; or a (C1-C4) alkylsulfonyl group substituted with at least one kind of group selected from the group consisting of a hydroxy group, a sulfo group, and a carboxy group.

2. The azo compound, the tautomer thereof, or the salt of the azo compound or the tautomer according to claim 1, wherein the azo compound represented by the formula (1) is represented by the following formula (2):

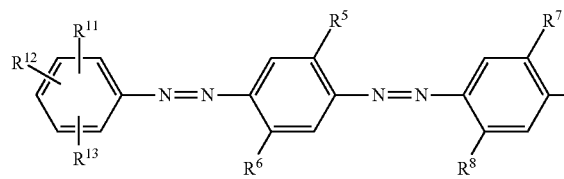
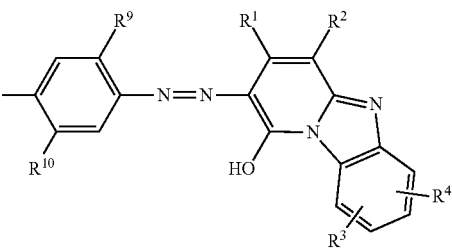

wherein, $R^1$ to $R^{13}$ respectively have the same meanings as defined in the formula (1).

3. The azo compound, the tautomer thereof, or the salt of the azo compound or the tautomer according to claim 1, wherein in the formula (1) at least one of $R^{11}$ to $R^{13}$ represents a sulfo group; or a carboxy group, and at least one of $R^5$ and $R^7$ represents a (C1-C4) alkylthio group substituted with a sulfo group or a carboxy group.

4. The azo compound, the tautomer thereof, or the salt of the azo compound or the tautomer according to claim 1, wherein in the formula (1), $R^5$ and $R^7$ each represents a (C1-C4) alkylthio group substituted with a sulfo group or a carboxy group, and $R^9$ represents a sulfo-(C1-C4) alkoxy group.

5. The azo compound, the tautomer thereof, or the salt of the azo compound or the tautomer according to claim 1, wherein in the formula (1), $R^1$ represents a methyl group; or a phenyl group, $R^2$ represents a cyano group; or a carbamoyl group, $R^3$ represents a hydrogen atom; a methyl group; or a methoxy group, and $R^4$ represents a sulfo group.

6. The azo compound, the tautomer thereof, or the salt of the azo compound or the tautomer according to claim 1, wherein in the formula (1), $R^1$ represents a methyl group; or a phenyl group;
$R^2$ represents a cyano group; or a carbamoyl group;
$R^3$ represents a hydrogen atom; a methyl group; or a methoxy group;
$R^4$ represents a sulfo group;
$R^5$ represents a (C1-C4) alkylthio group substituted with a sulfo group or a carboxy group;
$R^6$ represents a (C1-C4) alkylcarbonylamino group;
$R^7$ represents a (C1-C4) alkylthio group substituted with a sulfo group or a carboxy group;
$R^8$ represents a (C1-C4) alkylcarbonylamino group;
$R^9$ represents a sulfo-(C1-C4) alkoxy group;
$R^{10}$ represents a (C1-C4) alkyl group; or an acetylamino group; and
$R^{11}$ to $R^{13}$ each independently represents a hydrogen atom; a carboxy group; a sulfo group; a chlorine atom; a nitro group; a methyl group; a methoxy group; a sulfamoyl group; or a (C1-C4) alkylsulfonyl group substituted with a sulfo group or a carboxy group.

7. The azo compound, the tautomer thereof, or the salt of the azo compound or the tautomer according to claim 1, wherein in the formula (1), $R^1$ represents a methyl group
$R^2$ represents a cyano group or a carbamoyl group;
$R^3$ represents a hydrogen atom; a methyl group; or a methoxy group;
$R^4$ represents a sulfo group;
$R^5$ represents a sulfo-(C1-C4) alkylthio group;
$R^6$ represents a (C1-C4) alkylcarbonylamino group;
$R^7$ represents a sulfo-(C1-C4) alkylthio group;
$R^8$ represents a (C1-C4) alkylcarbonylamino group;
$R^9$ represents a sulfo-(C1-C4) alkoxy group;
$R^{10}$ represents a (C1-C4) alkyl group; or an acetylamino group; and
$R^{11}$ to $R^{13}$ each independently represents a hydrogen atom; a carboxy group; a sulfo group; a chlorine atom; a nitro group; a methyl group; a methoxy group; or a sulfamoyl group.

8. The azo compound, the tautomer thereof, or the salt of the azo compound or the tautomer according to claim 1, wherein in the formula (1), $R^1$ represents a methyl group;
$R^2$ represents a cyano group;
$R^3$ represents a hydrogen atom; or a methoxy group;
$R^4$ represents a sulfo group;
$R^5$ represents a sulfo-(C1-C4) alkylthio group;
$R^6$ represents an acetylamino group;
$R^7$ represents a sulfo-(C1-C4) alkylthio group;
$R^8$ represents an acetylamino group;
$R^9$ represents a sulfopropoxy group; or a sulfobutoxy group;
$R^{10}$ represents a (C1-C4) alkyl group;
$R^{11}$ represents a hydrogen atom; or a sulfo group;
$R^{12}$ represents a sulfo group; or a chlorine atom; and
$R^{13}$ represents a hydrogen atom; or a sulfo group.

9. An aqueous ink composition comprising, as a coloring matter, at least one kind of the azo compound, the tautomer thereof, or the salt of the azo compound or the tautomer according to claim 1.

10. The aqueous ink composition according to claim 9, further comprising a water-soluble organic solvent.

11. An inkjet recording method, comprising using utilizing the ink composition according to claim 9 as an ink; and discharging ink droplets of the ink according to recording signals, thereby performing recording on a record-receiving material.

12. The inkjet recording method according to claim 11, wherein the record-receiving material is a communication sheet.

13. The inkjet recording method according to claim 12, wherein the communication sheet is a sheet having an ink-receiving layer containing a porous white inorganic substance.

14. An inkjet printer equipped with a vessel containing the ink composition according to claim 9.

15. A colored material, colored with the azo compound, the tautomer thereof, or the salt of the azo compound or the tautomer according claim 1.

16. A colored material colored with the aqueous ink composition according to claim 9.

17. A colored material colored with the inkjet recording method according to claim 11.

* * * * *